United States Patent
Stoiber et al.

(10) Patent No.: US 12,385,899 B2
(45) Date of Patent: Aug. 12, 2025

(54) NANOPORE SEQUENCING BASE CALLING

(71) Applicant: THE REGENTS OF THE UNIVERSITY OF CALIFORNIA, Oakland, CA (US)

(72) Inventors: Marcus Stoiber, Napa, CA (US); James Brown, El Sobrante, CA (US)

(73) Assignee: The Regents of the University of California, Oakland, CA (US)

( * ) Notice: Subject to any disclaimer, the term of this patent is extended or adjusted under 35 U.S.C. 154(b) by 185 days.

(21) Appl. No.: 16/325,357

(22) PCT Filed: Jul. 10, 2017

(86) PCT No.: PCT/US2017/041395
§ 371 (c)(1),
(2) Date: Feb. 13, 2019

(87) PCT Pub. No.: WO2018/034745
PCT Pub. Date: Feb. 22, 2018

(65) Prior Publication Data
US 2019/0204296 A1  Jul. 4, 2019

Related U.S. Application Data

(60) Provisional application No. 62/491,960, filed on Apr. 28, 2017, provisional application No. 62/376,832, filed on Aug. 18, 2016.

(51) Int. Cl.
*G01N 33/487* (2006.01)
*C12Q 1/68* (2018.01)
(Continued)

(52) U.S. Cl.
CPC ......... *G01N 33/48721* (2013.01); *C12Q 1/68* (2013.01); *C12Q 1/6869* (2013.01);
(Continued)

(58) Field of Classification Search
CPC .. G01N 33/48721; G16B 30/00; G16B 40/00; G16B 50/00; C12Q 1/6869;
(Continued)

(56) References Cited

U.S. PATENT DOCUMENTS

2015/0057948 A1  2/2015 Reid et al.
2017/0370903 A1* 12/2017 Mager .............. G01N 27/44791

FOREIGN PATENT DOCUMENTS

WO  WO2014205401 A1  12/2014

OTHER PUBLICATIONS

Boza, Vladimir; Brejova, Brona; Vinar, Tomas. arXiv:1603.09195. Posted Mar. 30, 2016.*
(Continued)

*Primary Examiner* — Olivia M. Wise
*Assistant Examiner* — Janna Nicole Schultzhaus
(74) *Attorney, Agent, or Firm* — Dickinson Wright PLLC

(57) ABSTRACT

Disclosed herein are systems and methods for nanopore sequencing basecalling. In one embodiment, the method can include: receiving raw nanopore sequencing data comprising a plurality of continuous data acquisition (DAC) values corresponding to a biomolecule; normalizing the raw nanopore sequencing data to generate normalized nanopore sequencing data comprising a plurality of normalized DAC values; generating, using a first neural network (NN) and a normalized DAC value of the plurality of normalized DAC values, a vector of transformed probability values, segmenting the plurality of normalized DAC values into a plurality of discrete events; generating, using a second neural network and the event vector, an element determination of the biomolecule.

24 Claims, 18 Drawing Sheets

Specification includes a Sequence Listing.

(51) Int. Cl.
- *C12Q 1/6869* (2018.01)
- *G16B 20/20* (2019.01)
- *G16B 30/00* (2019.01)
- *G16B 40/00* (2019.01)
- *G16B 40/10* (2019.01)
- *G16B 50/00* (2019.01)

(52) U.S. Cl.
CPC .............. *G16B 20/20* (2019.02); *G16B 30/00* (2019.02); *G16B 40/00* (2019.02); *G16B 40/10* (2019.02); *G16B 50/00* (2019.02); *C12Q 2563/116* (2013.01); *C12Q 2565/631* (2013.01)

(58) Field of Classification Search
CPC ........ C12Q 2563/116; C12Q 2565/631; C12Q 2537/165
See application file for complete search history.

(56) References Cited

OTHER PUBLICATIONS

Winters-Hilt, S., Vercoutere, W., DeGuzman, V.S., Deamer, D., Akeson, M. and Haussler, D., Highly accurate classification of Watson-Crick basepairs on termini of single DNA molecules. Biophysical Journal, 84(2), pp. 967-976. (Year: 2003).*

Hochreiter, S. and Schmidhuber, J., Long short-term memory. Neural computation, 9(8), pp. 1735-1780. (Year: 1997).*

McIntyre, Alexa; Alexander, Noah; Burton, Aaron; Castro-Wallace, Sarah; Chiu, Charles; John, Kristen; Stahl, Sarah; Li, Sehng; Mason, Christopher. bioRxiv:10.1101/127100. Posted Apr. 13, 2017.*

Schreiber, J., Wescoe, Z.L., Abu-Shumays, R., Vivian, J.T., Baatar, B., Karplus, K. and Akeson, M. Error rates for nanopore discrimination among cytosine, methylcytosine, and hydroxymethylcytosine along individual DNA strands. Proceedings of the National Academy of Sciences, 110(47), pp. 18910-18915. (Year: 2013).*

International Search Report and Written Opinion issued in PCT Patent Application No. PCT/US17/41395 dated Oct. 3, 2017, pp. 1-15.

Boza, V, et al., DeepNano: Deep Recurrent Neural Networks For Base Calling In Min/ON Nanopore Reads. arXiv. Mar. 30, 2016, pp. 1-12.

Ip, CLC, et al. MiniION Analysis and Reference Consortium: Phase 1 Data Release and Analysis [Version 1; Referees: 2 Approved]. F1 000 Research. Oct. 15, 2015, pp. 1-35.

Stobier & Brown, "BasecRAWller: Streaming Nanopore Basecalling Directly from Raw Signal," bioRxiv 2017, in 15 pages. doi: https://doi.org/10.1101/133058;.

Stobier et al., "De novo Identification of DNA Modifications Enabled by Genome-Guided Nanopore Signal Processing," bioRxiv 2016, in 25 pages. doi: https://doi.org/10.1101/094672;.

* cited by examiner

SEQUENCE LISTING

<160> NUMBER OF SEQ ID NOS: 2

<210> SEQ ID NO 1
<211> LENGTH: 20

```
<212> TYPE: DNA
<213> ORGANISM: Artificial Sequence
<220> FEATURE:
<223> OTHER INFORMATION: Partial sequence of a DNA strand threading
      through a microscopic pore in a membrane

<400> SEQUENCE: 1
tgatattgct tttgatgccg                                             20

<210> SEQ ID NO 2
<211> LENGTH: 12
<212> TYPE: DNA
<213> ORGANISM: Artificial Sequence
<220> FEATURE:
<223> OTHER INFORMATION: Bases called

<400> SEQUENCE: 2
ccaagaatgt tt                                                     12
```

NANOPORE SEQUENCING BASE CALLING

RELATED APPLICATION

The present application is a U.S. national phase application under 35 U.S.C. § 371 of International Application No. PCT/US2017/041395, filed on Jul. 10, 2017 and published on Feb. 22, 2018, which claims priority to U.S. Provisional Application No. 62/376,832, filed on Aug. 18, 2016; and U.S. Provisional Application No. 62/491,960, filed on Apr. 28, 2017. The content of each of these related applications is hereby expressly incorporated by reference in its entirety.

STATEMENT REGARDING FEDERALLY SPONSORED R&D

This invention was made with government support under grant No. DE-AC02-05CH11231 awarded by the U.S. Department of Energy. The government has certain rights in the invention.

REFERENCE TO SEQUENCE LISTING

The present application includes a Sequence Listing in electronic format. The Sequence Listing is provided as a file entitled Sequence_Listing_69DW-302580-US, created Mar. 25, 2022, which is 1 kilobyte in size. The information in the electronic format of the Sequence Listing is incorporated herein by reference in its entirety.

BACKGROUND

Field

The present disclosure relates generally to the field of DNA sequencing, and more particularly to basecalling for nanopore sequencing.

Description of the Related Art

Current nanopore sequencing devices (e.g., MinION from Oxford Nanopore Technologies (Oxford, United Kingdom)) can measure the nucleotide sequence of DNA (or RNA). This process begins by the measurement of electric current across a nanopore as strand of DNA passes through the pore. These measurements can be stored as 16-bit integer data acquisition (DAC) values, currently taken at 4 kHz frequency. With a DNA strand velocity of ~450 base pairs per second, this gives approximately nine raw observations per base on average. This signal can then be processed to identify breaks in the open pore signal corresponding to individual reads. These stretches of raw signal are base-called—the process of converting DAC values into a sequence of DNA bases that is a prerequisite for essentially all applications of nanopore technology.

Extant basecalling systems, albacore (ONT), Nanocall (e.g., David, M., et al. Nanocall: an open source basecaller for Oxford Nanopore sequencing data. Bioinformatics 33, 49-55 (2017), the content of which is hereby incorporated by reference in its entirety), and DeepNano (e.g., Vladimír Boža, B.B., et al. DeepNano: Deep Recurrent Neural Networks for Basecalling in MinION Nanopore Reads. arXiv (2016), the content of which is hereby incorporated by reference in its entirety), generally begin with the same initial processing step, such to segment the DAC values into "events" that ideally represent individual nucleotides. These events are then processed with either a hidden markov model (HMM; Nanocall and previous versions of ONT basecallers) or a recurrent neural network (RNN; albacore and DeepNano) to predict the sequence of an oligonucleotide in and near the center of the pore associated with each event. An oligonucleotide with a length of k can be referred to as a k-mer or a k-base oligonucleotide. These values are subsequently resolved with neighboring events to produce a complete sequence for each read. For example, a nanopore basecalling application can begin with the segmentation of raw signals into discrete events, which are ultimately processed into called bases. A current event or base segmentation can be done using a t-test and computation for basecalling can be performed on the mean and SD of these segments.

SUMMARY

Disclosed herein are systems and methods for nanopore sequencing basecalling. In one example, the system includes a computer-readable memory storing executable instructions; and one or more hardware-based processors programmed by the executable instructions to perform a method comprising: receiving raw nanopore sequencing data comprising a plurality of continuous data acquisition (DAC) values corresponding to a biomolecule; normalizing the raw nanopore sequencing data to generate normalized nanopore sequencing data comprising a plurality of normalized DAC values; generating a vector of transformed probability values using a first neural network (NN) and a normalized DAC value of the plurality of normalized DAC values; and determining a base in the biomolecule based on the generated vector of transformed probability vectors.

BRIEF DESCRIPTION OF THE DRAWINGS

FIG. 12A is a scatter plot that shows the correlation between the median signal level before a read and within a nanopore read. FIG. 12B is a signal plot that shows non-limiting exemplary reads of the correlated data showing that these values include an open pore signal.

DETAILED DESCRIPTION

Figure 1:
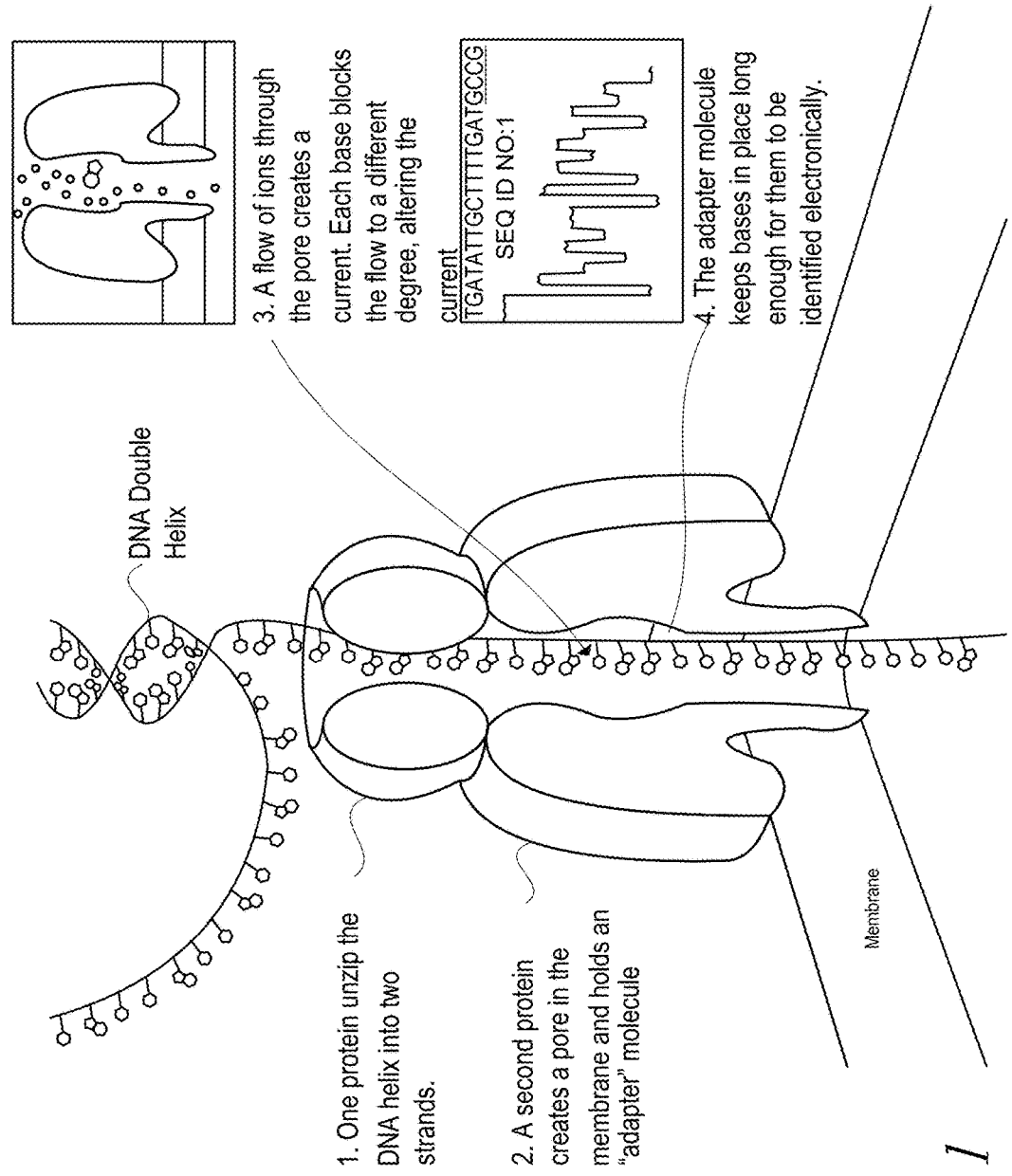
FIG. 1 is a schematic illustration of determining the sequence of DNA fragments by passing DNA through a protein (or other) pore in a membrane.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein is a "basecRAWller" system, method, process, or workflow which can include a pair of unidirectional recurrent neural networks that enables the calling of DNA bases in real time directly from the rawest form of output from a nanopore. The basecRAWller system, method, or workflow can integrate basecalling and segmentation directly from the raw data via a recurrent neural network (RNN) to achieve an improvement in accuracy speed, and throughput. This method of nanopore basecalling may provide one or more of the following advantages over current processing pipelines including: 1) streaming basecalling, 2) tunable ratio of insertions to deletions, and 3) potential for streaming detection of modified bases. Streaming basecalling can involve sequence prediction at a delay of less than 1/100th of a second during the run. The basecRAWller process is computationally efficient, enabling basecalling at relatively high speeds compared to current systems using a single processor core. Further, the system can be paused and resumed without any change in the resulting predicted sequence, presenting the potential to enhance the efficiency of nanopore sequencing dynamic read rejection capabilities. The basecRAWller process can provide an alternative approach to nanopore basecalling at comparable accuracy and provide users with the capacity to train their own basecRAWller neural networks with minimal effort.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, NY 1989).

Overview

Disclosed herein are improved systems and methods for basecalling. In some embodiments, the basecalling method (e.g., the basecRAWller process) can shift the nanopore basecalling paradigm by deferring segmentation into events until after sequence content is analyzed. By utilizing only unidirectional (forward in sequencing time) recurrent neural networks (or another type of neural network), a system implementing the basecRAWller process can predict bases in a streaming fashion, directly from raw nanopore sequencing data. Other extant basecallers can require a full pass over the signal to produce final basecalls. Single reads can approach 1 MB (e.g., lab.loman.net/2017/03/09/ultrareads-for-nanopore/) and at DNA translocation speed of 450 bp/see, a single read can take over half an hour to sequence. Thus accurate streaming basecalling can be beneficial for several applications, especially those related to dynamic read rejection (e.g., Loose, M., et al. Real-time selective sequencing using nanopore technology. Nat Methods 13, 751-754 (2016), the content of which is hereby incorporated by reference in its entirety).

A neural network can directly applied to the transformed raw signal for basecalling (referred to herein as a raw net). In some embodiments, two neural networks can be applied to nanopore sequencing data: the raw net can be applied directly to the raw signal or normalized raw signal, and the second neural network (referred to herein as a fine-tune net) can be applied after segmentation of the output of the raw net into approximate base pairs. The combination of these two neural networks for basecalling of nanopore sequencing data can have an improved performance.

Basecalling for the nanopore sequencing technology can be based on long short-term memory (LSTM) recurrent neural networks (RNNs). In some embodiments, a LSTN-RNN basecaller can include one or more bidirectional LSTM layers, feed forward layers, and soft max layers. The output of a LSTN-RNN basecaller can be a posterior matrix of probabilities of oligonucleotides, such as 3-, 4-, 5-, or 10-mers. A LSTM-RNN basecaller can have accuracy improvements compared to a basecaller based on a Hidden Markov Modes. A LSTM-RNN basecaller can be tuned for performance and speed. A LSTM-RNN basecaller can implement z-scaling, such as normalization based on z-scores. Challenges for nanopore sequencing include the need to segment signals or raw data into individual events representing base pairs and determine to which base each event corresponds.

Nanopore Sequencing

One advantage of the nanopore sequencing technology can be that DNA sequencers based on the nanopore sequencing technology can be compact and transportable. Some industries that can benefit from the nanopore sequencing technology and the methods of the present disclosure include agriculture & farming, waste and water treatment processing, personal medicine, disease outbreak, biofuels, or basic biological research. Basecalling based on the methods disclosed herein can allow greater accuracy and offline basecalling. The number of industries that would benefit from the methods of the present disclosure are numerous.

The nanopore sequencing technology can be applicable to sequencing of biological materials.

FIG. 1 is a schematic illustration of determining the sequence of DNA fragments by passing DNA through a protein (or other) pore in a membrane. An example implementation of determining the sequence of DNA fragments by passing DNA through a protein (or other) pore in a member is the nanopore sequencing technology. The nanopore sequencing technology can be single molecule-based. DNA can be sequenced by threading it through a microscopic pore in a membrane. Bases can be identified by the way they affect ions flowing through the pore from one side of the membrane to the other. One protein molecule can unzip the DNA helix into two strands. A second protein can create a pore in the membrane and hold an "adapter" molecule. A flow of ions through the pore can create a current. Each base can block the flow of ions to a different degree, altering the current. The adapter molecule can keep bases in place long enough for them to be identified electronically.

The nanopore sequencing technology can be applicable to sequencing of biological materials. One advantage of the nanopore sequencing technology can be that DNA sequencers based on the nanopore sequencing technology can be compact and transportable. Some industries that can benefit from the nanopore sequencing technology and the methods of the present disclosure include agriculture & farming, waste and water treatment processing, personal medicine, disease outbreak, biofuels, or basic biological research. Advantages of the nanopore sequencing technology include the long read length, potential for direct RNA sequencing, sequencing for biological problems with data velocity issues. For example, ~400 GB/24 hours may need to be processed. The nanopore sequencing technology can be a cost-effective method for DNA sequencing.

Figure 2:
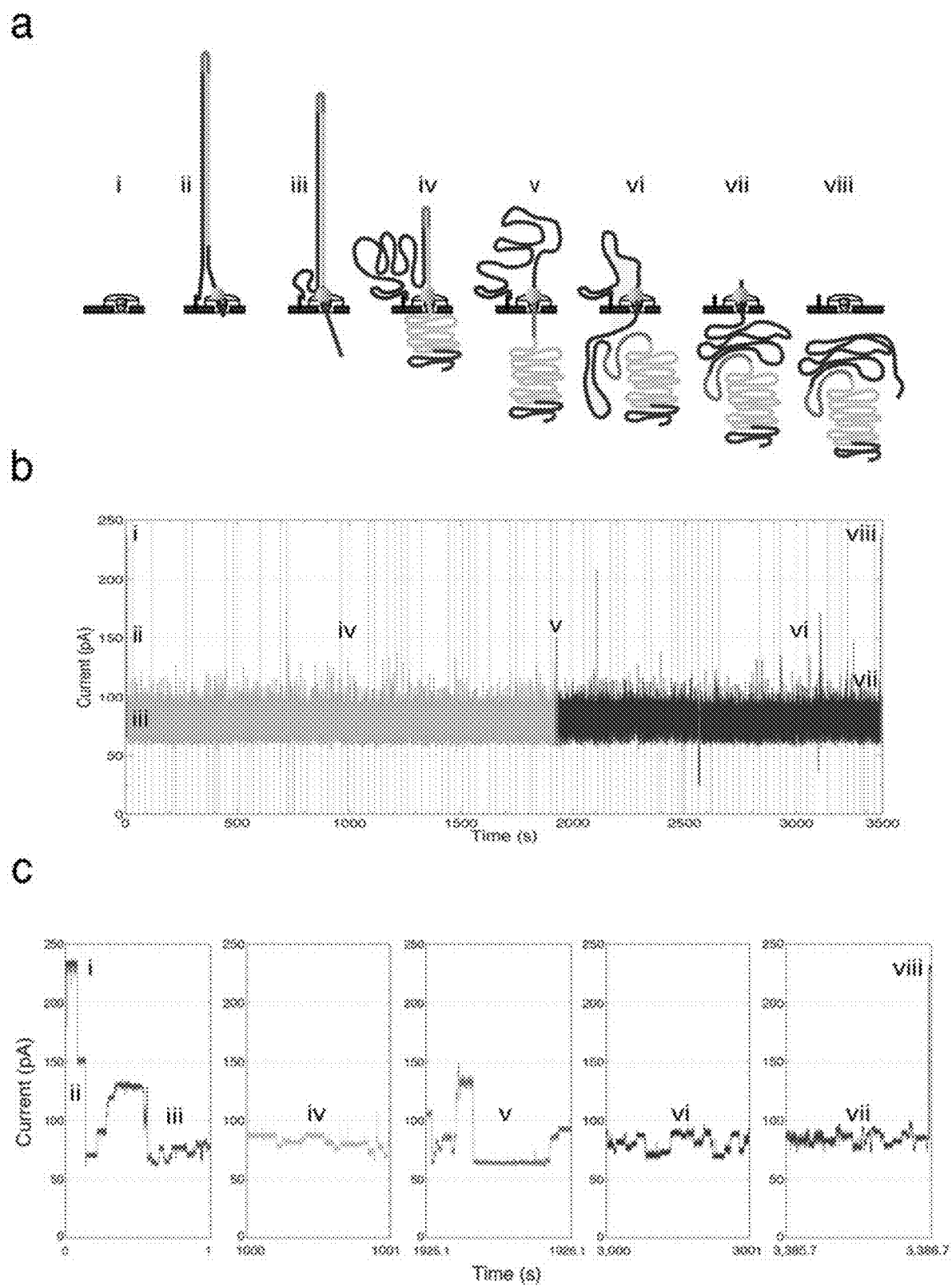
FIG. 2 shows Data for a 2D read of a full-length 2 phage dsDNA from the MinION.

FIG. 2 shows data for a two dimensional (2D) read of a full-length λ phage dsDNA from the MinION. FIG. 2, panel a shows schematic illustration of the nanopore sequencing technology. Molecular events for translocation of a single 48-kb λ dsDNA molecule through the MinION nanopore sequencer. DNA length and conformation are simplified for purposes of illustration. (i) Open channel. (ii) dsDNA with ligated loading (blue and brown) and hairpin adaptors (red) captured by the nanopore with the aid of a membrane anchor and an applied voltage across the membrane. (iii) Translocation of 5' end of the loading adaptor through the nanopore under control of a molecular motor and driven by the applied potential across the membrane. DNA translocation through the nanopore starts. (iv) Translocation of the template strand of DNA (gold). (v) Translocation of the hairpin adaptor (red). (vi) Translocation of the complement strand (blue). (vii) Translocation of 3' portion of the loading adaptor. (viii) Return to open-channel nanopore. FIG. 2, panel b shows raw current trace for the entire passage of the DNA construct through the nanopore (approximately 2,789 s). Regions of the ionic current trace corresponding to steps i-viii are labeled. FIG. 2, panel c shows example expanded 1-s time scale of raw current traces for DNA capture and translocation of 5' loading adaptors (i-iii), template strand (iv), hairpin adaptor (v), complement strand (vi), 3' loading adaptor and return to open channel (vii-viii). Each adaptor generates a unique signal used for position reference in base determination.

With nanopore sequencing, 50 or more base pairs, such as 250-400 base pairs with a R9 pore, per second can pass through a pore. Challenges for nanopore sequencing include the need to segment signals or raw data into individual events representing base pairs and determine to which base each event corresponds. In some embodiments, the processing of nanopore sequencing data can include segmentation of the nanopore data, basecalling, and alignment to genome sequences. After segmentation, bases can be called prior to the sequences determined being aligned to reference genome data.

Noise level can be quite high for raw nanopore sequencing data. A plot overlaying raw nanopore sequencing data observed eight times for the same DNA sequence can show that the raw nanopore sequencing data can have a high noise level. With post correction and normalization distributions, some signal exists exist before complex machine learning. Around 13% accuracy can be achievable by nearest mean calculations for predicting 2-mers.

BasecRAWller Process

Figure 3:
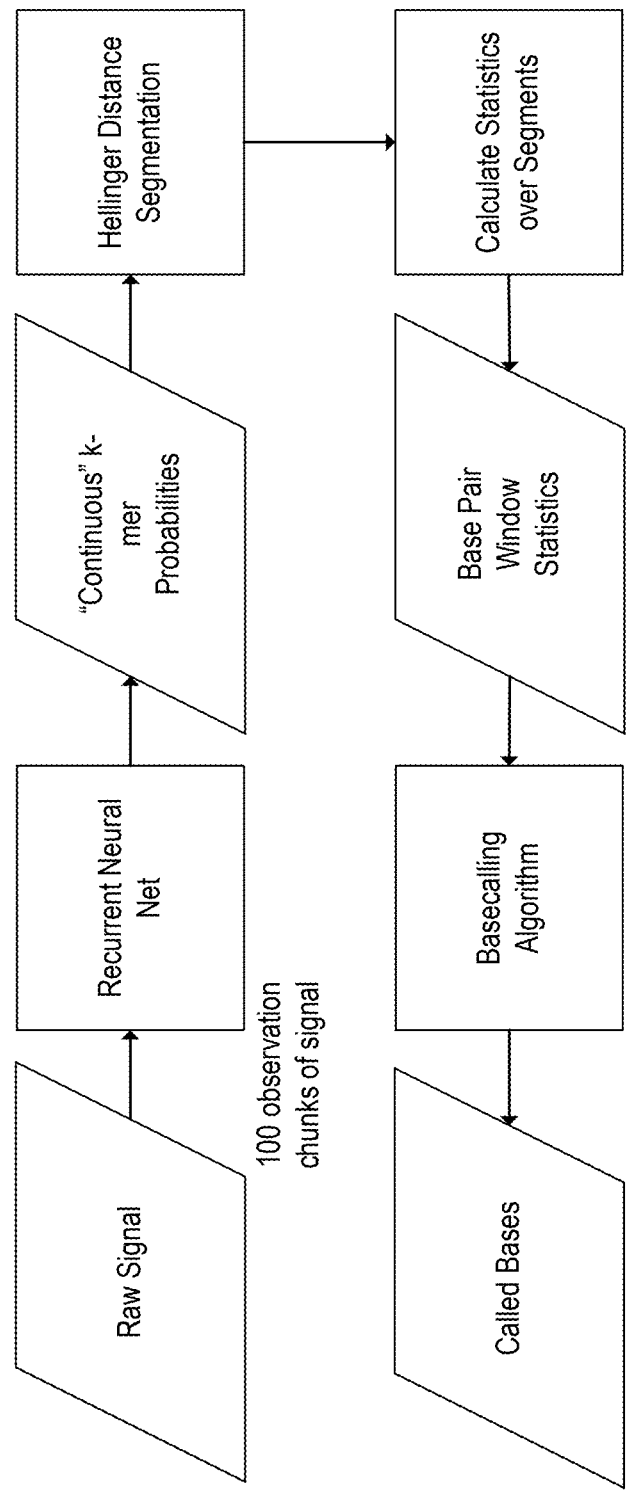
FIG. 3 shows an example process of basecalling.

FIG. 3 shows an example process of basecalling. The basecalling process receives raw signal and process it with a recurrent neural network. The input of the recurrent neural network can be normalized, for example, in a streaming manner. For example, read signal can be used to estimate a shift parameter for median normalization. As another example, a signal shift parameter can be determined from signal after open pore signal and before read start, thus enabling fully streaming basecalling. To enable fully streaming basecalling, the signal immediately before the read start can be utilized to estimate shift.

After determining "continuous" oligonucleotide probabilities and performing segmentation, statistics over segments can be calculated. Segmentation can include identifying peaks in splitting statistic using, for example, LSTM, Hellinger Distance, or Entropy Difference. Peaks within minimum distance of another higher peak can be removed. Global threshold to identify split locations can be applied to identify split locations. For example, global threshold can be determined from nanoraw true base counts, and the number of identified splits error over many reads can be minimized. Oligonucleotide probabilities, such as 4-mer probabilities, over each segment can be averaged. Thus, the segmentation method can be completely stream-able.

The basecalling system or process can call bases after determining base pair window statistics. Advantages of the basecalling method of the present disclosure include the ability to process the large amount of data generated. Further, accuracy of the basecalling method disclosed herein has a high accuracy to provide meaningful biological insight. Further, the method can interrogate the data in order to assess confidence as well as possible alterations outside of the given model. Furthermore, base alterations (e.g., methylation, acetylation, etc.) can be investigated via encoding layers.

The basecalling method disclosed herein is configured to solve the problem of interpreting electric current-based readout measured from biological materials (DNA, RNA or protein) passing through a nanopore in a membrane. The method may not implement Hidden Markov Models (HMM) which require a large amount of computational time and large amounts of memory and thus cannot be computed on a personal computer.

In one embodiment, the method can read in the current-based measurements through time into a trained recurrent neural network in order to predict the probability that the current measurement is derived from a particular oligonucleotide, where a oligonucleotide represents the k most recent nucleic acids (DNA and RNA) or amino acids (proteins). The probabilities are then segmented based only on these probabilities and passed to a second neural network. This second neural network takes in the arrays of probabilities through time and produces probabilities of the final sequence for each segment, again either nucleic acids or amino acids. This data is output in industry standard formats (FASTA and FASTQ) and made available for standard downstream bioinformatics processing.

Training data set can be obtained using the HMM-based basecaller provided from Oxford Nanopore Technologies (Oxford, United Kingdom) based on cDNA libraries from *E. coli*. The processing of this data to produce useful input for training is non-trivial and requires advanced bioinformatic expertise including mapping long reads and aligning the raw electric current signal through called events to an alignment to an appropriate genome. The construction of the two neural networks can require statistical and computational expertise. These neural networks can be implemented using the Caffe program developed at UC Berkeley and specifically the git fork #2033 which implements LSTM layers into Caffe or with the tensorflow python package interface again using LSTMs. The segmentation of the produced probabilities from the first neural network can require statistical and computational expertise.

Embodiments of methods disclosed herein may be able to overcome hurdles in the field of the nanopore sequencing technology and allow for an advance in the potential uses as well as the validity of the results from this type of data. One advantage of the method is the ability to process data locally on a personal computer. Raw data may not need to be uploaded to a high performance server in order to be processed and is then returned to the user in a useful format for biological processing.

An example method of correcting for deletions in raw nanopore sequencing data can include the following steps. First, center on deletion. Second, expand to neighboring regions. Third, segment using mean changepoint. An example method of correcting for insertions in raw nanopore sequencing data can include the following steps. First, center on insertion. Second, expand to neighboring regions. Third, segment using mean changepoint. An example complex corrections of raw nanopore sequencing data can include the following steps. First, determine if multiple corrections "intersect." Second, expand selection to entire region. Third, segment using mean changepoint.

BasecRAWller Architecture

Basecalling for the nanopore sequencing technology can be based on long short-term memory (LSTM) recurrent neural networks (RNNs). In some embodiments, a LSTN-RNN basecaller can include one or more bidirectional LSTM layers, feed forward layers, and soft max layers. A layer can include 16, 32, 64, 128, or more layers. The input of a LSTN-RNN basecaller can be a 12-dimensional input vector. The output of a LSTN-RNN basecaller can be a posterior matrix of probabilities of oligonucleotides, such as 3-, 4-, 5-, or 10-mers. A LSTM-RNN basecaller can have accuracy improvements compared to a basecaller based on a Hidden Markov Modes. A LSTM-RNN basecaller can be tuned for performance and speed. A LSTM-RNN basecaller can implement z-scaling, such as normalization based on z-scores. The nanopore sequencing technology can be based on R7 or R9 chemistry. The technology based on the R9 chemistry and RNNs can be fast, up to 500 bps/sec. The error rate based on the nanopore sequencing technology can be low, for example 26% error rate (for 2D reads) or 37% error for 1D reads.

Figure 4:
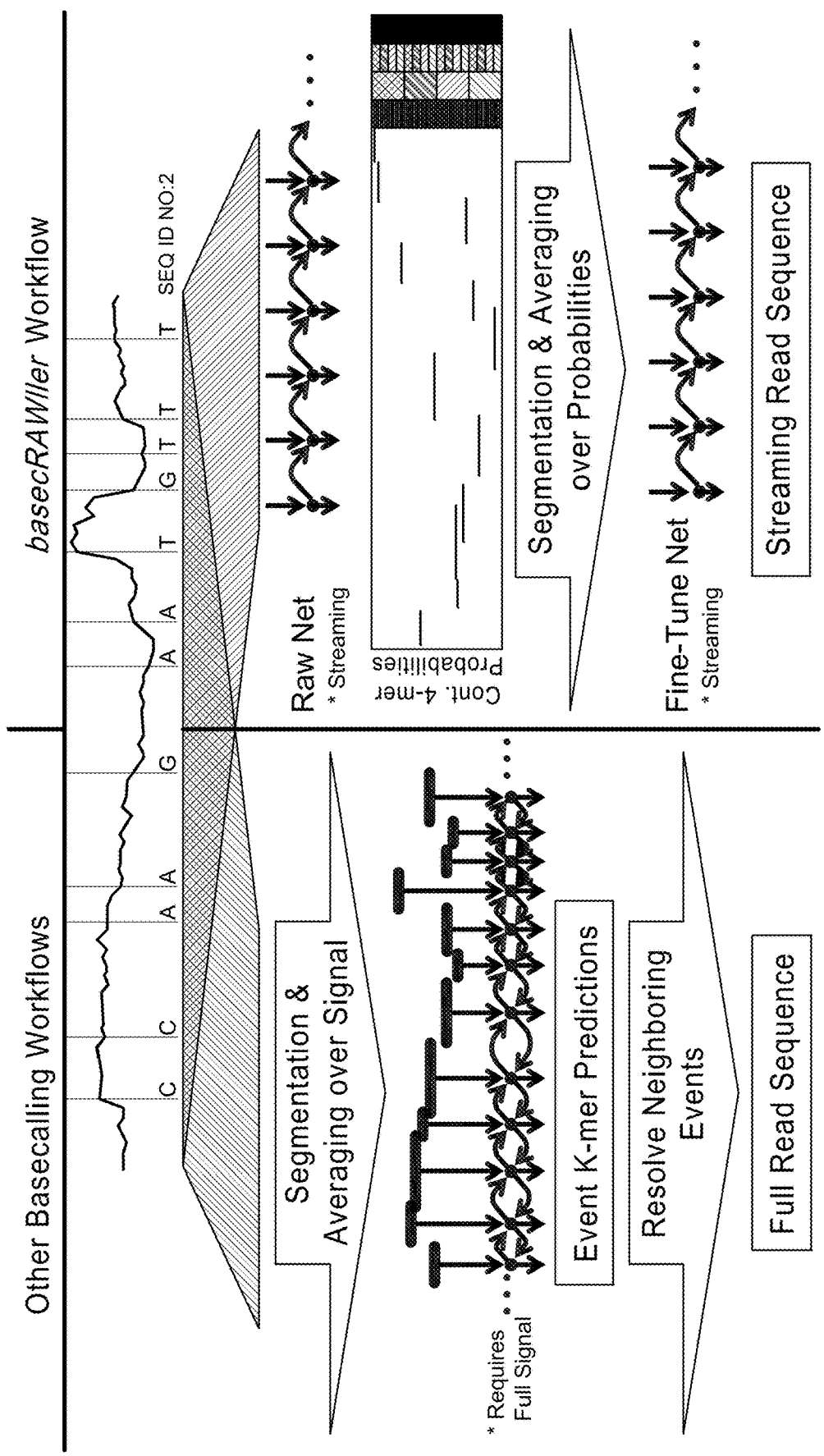
FIG. 4 shows a comparison of a current basecalling process with the basecRAWller process.

In one embodiment, the basecalling system and method disclosed herein (e.g., the basecRAWller system, method, process, or workflow) can be based on a pair of recurrent neural networks, referred to as the raw and fine-tune nets (FIG. 4).

Raw Net. The raw net can include several stacked long short term memory (LSTM) units (e.g., Hochreiter, S. et al. Long short-term memory. Neural Comput 9, 1735-1780 (1997), the content of which is hereby incorporated by reference in its entirety) followed by several fully connected layers. This network can take in scaled DAC values and outputs multinomial logit predictions for each 4-mer associated with each observation. In some embodiments, these predictions can be made at a delay of 33 raw observations (less than 1/100th of a second in sequencing time), which allows the network to take in signal at a brief lag past an observation before predicting the associated sequence allowing for modulation of the predicted sequence. This network can simultaneously output the probability that each observation corresponds to the beginning of a new base.

Figure 5A:
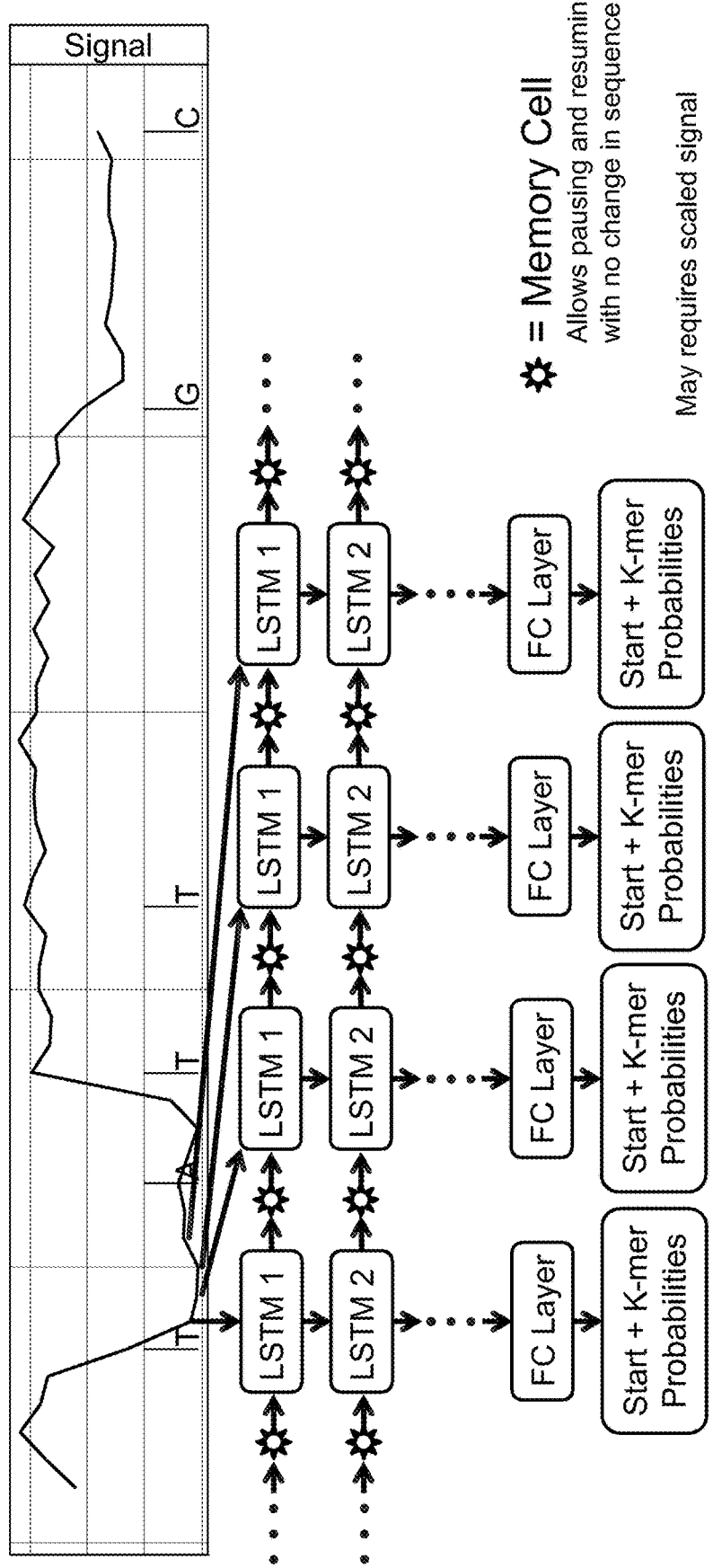
FIGS. 5A-5C show raw and fine-tuned neural network architectures. The raw net can include three LSTM layers and one fully connected (FC) layer, and the fine-tune net can include two LSTM layers and one FC layer. Probabilities can be generated at a delay in both nets, and the raw net can simultaneously predict the probability of a base starting at that observation. The input to the fine-tune net can be the segmented and averaged output logits from the raw net, and the output of the fine-tune net are the final sequences represented by each event.
Figure 5B:
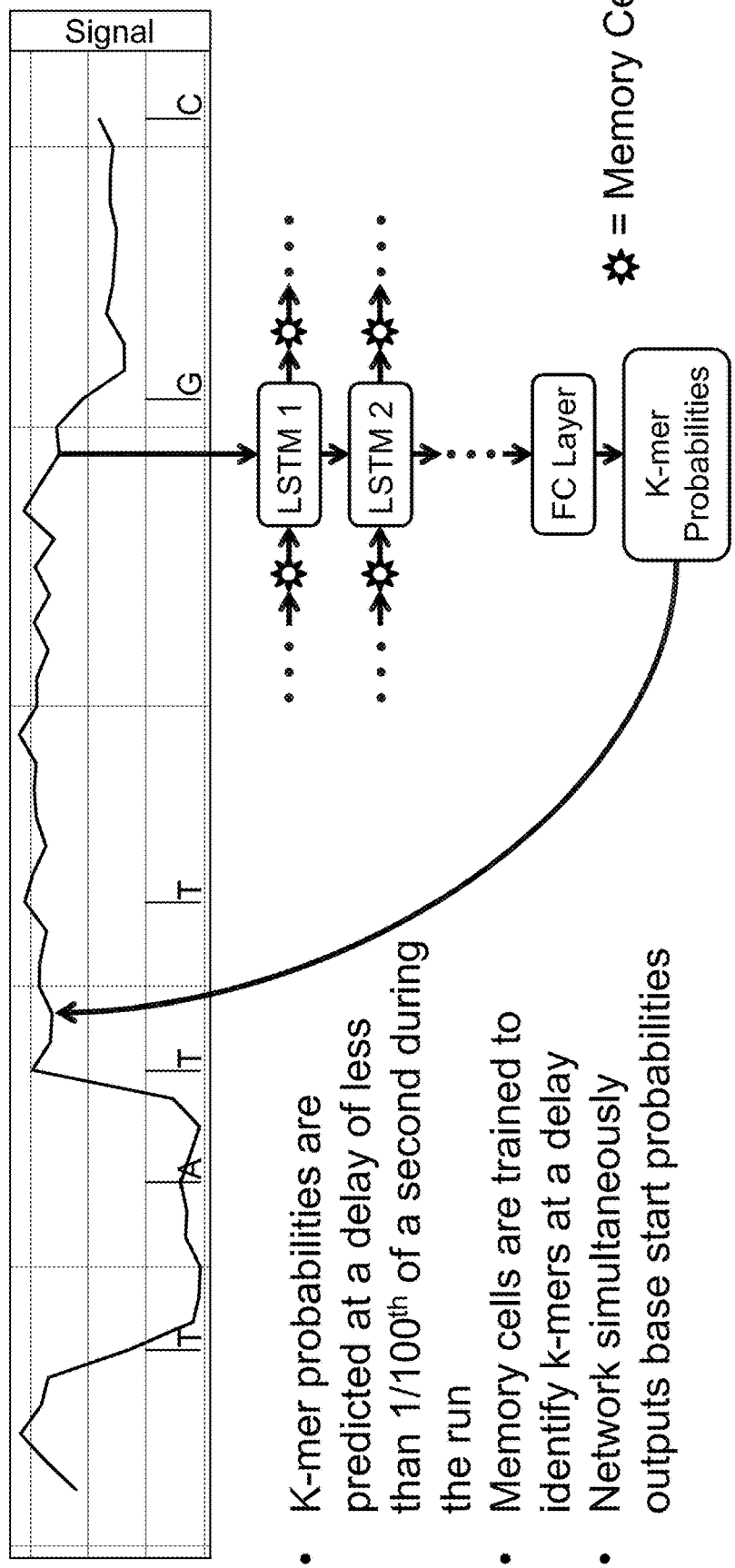

The raw net can include several stacked long short term memory (LSTM) units followed by several fully connected layers. FIGS. 5A-5B show one exemplary architecture of the raw net. This network can take as input a single scaled DAC value and return a vector of logits (transformed probability values) that any oligonucleotide is represented by a DAC value, as well a "memory" that is passed on to the next observation along with the next scaled DAC value. In parallel, the raw net output a logit value that this position is the beginning of a new base to be potentially used in the segmentation step. It should be realized that this network can be constructed with any number of LSTM layers, each with any number of output units (entered as a parameter during training). The oligonucleotide to predict can also be variable by specifying the number of bases before and after the current base to be included. The third layer can be added after training the two-layer network in order to more quickly identify appropriate parameters for the first two LSTM layers. The addition of a third LSTM layer after initial training of previous layers can improve overall neural network performance as well as optimization training computations since deeper layer training is susceptible to exploding and vanishing gradient problems. These problems can be alleviated by the training of the first (closer to the input) layers initially followed by training of these layers along with additional deeper layers. In some implementations, the raw net can produce, for each raw observation, a vector of logits representing the probability that this observation was derived from each distinct oligonucleotides along with a prediction that this position was the start of a new base.

Segmentation. A segmentation process can be applied to split the continuous sequence predictions into discrete events. For example, the 4-mer predictions, averaged over each event can then be passed to the fine-tune net to produce final sequence predictions, including small inserted bases (2 bases per event) and event deletion. These predictions can be made at a delay of two base pairs (approximately 0.005 seconds of sequencing time using the R9 technology) and the output of this neural network comprises the final predicted sequence from the basecRAWller system or process.

Segmentation can include identifying peaks in splitting statistic using, for example, LSTM, Hellinger Distance, or Entropy Difference. Peaks within minimum distance of another higher peak can be removed. Global threshold to identify split locations can be applied to identify split locations. For example, global threshold can be determined from nanoraw true base counts, and the number of identified splits error over many reads can be minimized. Oligonucleotide probabilities, such as 4-mer probabilities, over each segment can be averaged. Thus, the segmentation method can be completely stream-able.

Figure 5C:
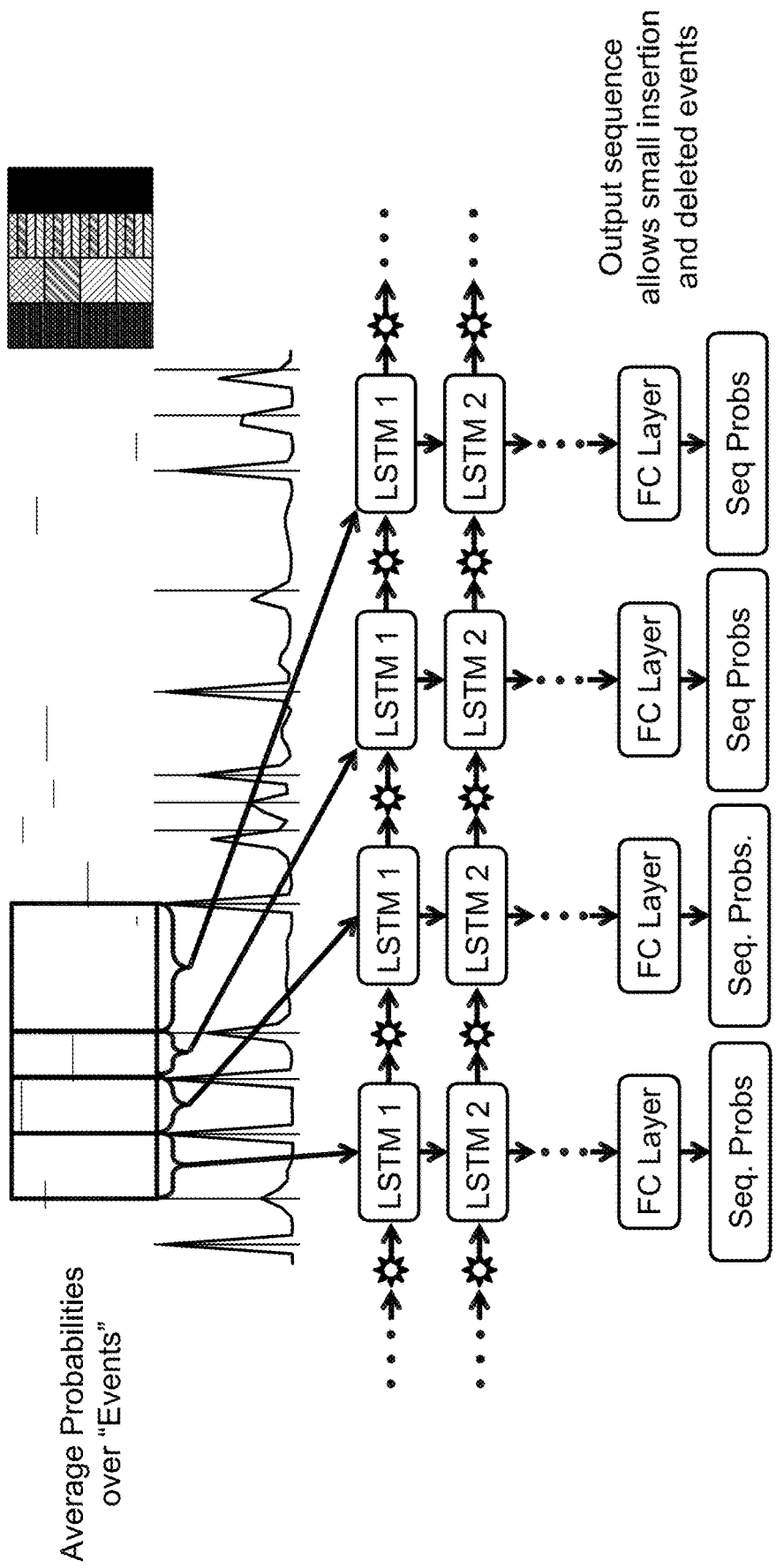

Fine-Tune Net. After raw net processing, segmentation and distribution averaging a second neural network can be applied to fine-tune the predicted bases from the raw net. The structure of the fine-tune net can be similar or identical to the raw net with some number of LSTM layers followed by one or more fully connected layers that output probability values. FIG. 5C shows an exemplary architecture of the fine-tune net. The differences can include that each observation taken in by the fine-tune net can be a vector of logits for each possible oligonucleotide instead of a single normalized DAC value and the output can be zero, one, two or three bases represented by this segment. The output of the fine-tune net can be the logit values for between 0 and some length of oligonucleotide that represents the bases to assign to the current segment. The 0-length state can indicate that the current segment should be deleted and should have been joined with the previous segment. The 1-mer state indicated that this segment has been correctly assigned a single base and specifies the specific base for that segment. The 2-mer and greater states indicate that the current segment represents more than one base (can be under segmented).

In one implementation, models can be trained based on each version of the nanopore technology or sample type and applied where applicable (including translocation speed, native versus amplified, ratchet protein and other workflow difference). Models can easily be shared amongst users enabled by the basecRAWller process. Additionally, particular parameters can be tuned to alter error profiles. For example the insertion penalty training parameter can produce basecRAWller models with a range of insertion to deletion ratios while maintaining similar match and mismatch ratios. In one implementation (basecRAWller version 0.1) the human data trained model can be the default provided with for the basecRAWller software (a software package implementing the basecRAWller process).

The basecRAWller process can be implemented as a command line software for training and running the basecRAWller model-based basecalling method. To call bases with a default model, the following command can be used:
>basecRAWller call--fast5-basedirs path/to/fast5s/\
--out-filename basecRAWller reads.fasta To call bases using a non-default model, the following command can be used:
>basecRAWller call--fast5-basedirs path/to/fast5s/\
--out-filename basecRAWller reads.fasta \
--raw-checkpoint-directory raw_checkpoints_dir/\
--ft-checkpoint-directory fine_tune_checkpoints_dir The non-default model can be generated be a user using the basecRAWller software.

In some implementations, parameters that can be optimized include: mean/median normalization (including+/− truncation), convolutional window size, predicted bases {2, 3, 4, or 5 bases}, loss function (include preference for current base), general recurrent neural network architecture, Rectified linear layer unit/dropout layers, or long short-term memory (LSTM) output nodes.

BasecRAWller Training

Training a basecRAWller model can include three processes: prepare and train a raw net; analyze splitting criterion; and prepare and train a fine-tune net. To prepare and train a raw net, the following command can be used:
>basecRAWller prep_raw_net
>basecRAWller train_raw_net To analyze splitting criterion, the following command can be used:
>basecRAWller analyze_splitting To prepare and train a fine-tune net, the following command can be used:
>basecRAWller prep_fine_tune_net
>basecRAWller train fine tune_net Considerations of BasecRAWller training include training run time/model robustness, which can be affected by parameters such as a number of reads, a number and size of layers, and a number of observations per iteration (num_unroll). Another consideration includes net accuracy versus final percent identity. Raw net reported accuracy can be per observation and fine-tune net reported accuracy can be categorical, so a predicted insertion may contain a single correct base. Loss may continue to decrease after accuracy has leveled off. However, some parameters make loss and accuracy un-comparable, such as a start prediction loss fraction for the raw net, and insertion to deletion ratio penalty for the fine-tune net. In some implementations, two LSTM layers can be trained first prior to a third layer, such as a fully connected layer, is added to the first layers.

BasecRAWller Parameters

Parameters of the basecRAWller process can be optimized. For example, parameters of one or more of the following types of parameters can be optimized: data preparation parameters, graph structure parameters, splitting parameters, training hyper-parameters, raw net hyper-parameters, and fine-tune net parameters. The data preparation parameters include a number of reads, a oligonucleotide prediction length (raw net), a maximum insertion size (fine-tune net) and a raw and events offset. The graph structure parameters include a number and size of LSTM layers and a number and size of fully connected layers. The splitting parameters include a measure lag, such as Hellinger distance and entropy, a minimum observations per base, and a number of split reads. The training hyper-parameters include a number of observations per training step, a learning rate, learning rate decay schedule, a parameter momentum, a total number of training iterations, and a dropout rate. The raw net hyper-parameters include a proportion of loss for start prediction and a start prediction mask size. The fine-tune net parameters include an insertion to deletion penalty. Different parameters can have different effects on accuracy. For example, the raw net offset can have a largest effect on accuracy. Recommended parameter ranges for user training can be provided in basecRAWller help commands.

Some of the parameters that can affect the performance, such as accuracy and speed, of the basecRAWller process are listed in Table 1. In one implementation, one or more of the following parameters can have high impact on the performance of the basecRAWller process: LSTM Sizes, Number of Unrolled Observations, Insertion Penalty, LSTM Sizes, and Observations Offset. One or more of the following parameters can have medium-high impact on the performance of the basecRAWller process: Number of Reads, Learning Rate, Start Proportion, Events Offset, Number of Unrolled Events, and Learning Rate. One or more of the following parameters can have medium impact on the performance of the basecRAWller process: Before Bases, After Bases, Fully Connected Sizes, Learning Rate Half Life, Total Iterations, Start Mask Size, Maximum Number of Inserted Bases, True Split Offset, Fully Connected Sizes, Learning Rate Half Life, and Total Iterations.

TABLE 1

Exemplary parameters of the basecRAWller process and their values and rainges.

| Parameter | Training Step | Selected Value | Recommended Range | Related Parameters |
|---|---|---|---|---|
| Before Bases | Raw Net | 1 | 1-4 | After Bases |
| After Bases | Raw Net | 2 | 1-6 | Before Bases |
| Observations Offset | Raw Net | 33 | 10-50 | Number of Unrolled Observations |
| Number of Reads | Raw Net | 10000 | >5000 | Trim Percent |
| Trim Percent | Raw Net | 50 | >10 | Number of Reads |
| LSTM Sizes | Raw Net | 75, 100, 50 | >25 | Fully Connected Sizes |
| Fully Connected Sizes | Raw Net | NA | >25 | LSTM Sizes, Kmer Bases |
| Number of Unrolled Observations | Raw Net | 500 | >150 | Kmer Bases, Fully Connected Sizes, LSTM Sizes |
| Learning Rate | Raw Net | 1 | 0.5-1.5 | |
| Learning Rate Half Life | Raw Net | 500 | 200-2000 | |
| Momentum | Raw Net | 0.9 | 0.8-0.96 | |
| Total Iterations | Raw Net | 5000 | >2000 | |
| Start Proportion | Raw Net | 1.1 | 0.7-1.5 | Kmer Bases, Learning Rate |
| Start Mask Size | Raw Net | 2 | 0-3 | |
| Keep Probability | Raw Net | 1 | 0.9-1.0 | |
| Measure Lag | Splitting | NA | 2 | |
| Minimum Observations per Base | Splitting | 4 | 2-6 | Measure Lag |
| Number of Split Reads | Splitting | 5000 | >1500 | |
| Max Observations per read | Splitting | 100000 | >20000 | |
| Maximum Number of Inserted Bases | Fine-Tune Net | 2 | 1-4 | Kmer Bases, Events Offset |
| True Split Offset | Fine-Tune Net | 3 | 1-6 | Maximum Number of Inserted Bases |
| Events Offset | Fine-Tune Net | 2 | 0-5 | Learning Rate |
| Insertion Penalty | Fine-Tune Net | 2 | 1.0-3.5 | |
| LSTM Sizes | Fine-Tune Net | 200, 75 | >50 | Fully Connected Sizes, Kmer Bases |
| Fully Connected Sizes | Fine-Tune Net | NA | >25 | LSTM Sizes, Maximum Number of Inserted Bases |
| Number of Unrolled Events | Fine-Tune Net | 90 | >75 | Events Offset |
| Learning Rate | Fine-Tune Net | 0.9 | 0.5-1.2 | |
| Learning Rate Half Life | Fine-Tune Net | 3000 | >1000 | |
| Momentum | Fine-Tune Net | 0.9 | 0.8-0.96 | |
| Total Iterations | Fine-Tune Net | 10000 | >5000 | |
| Keep Probability | Fine-Tune Net | 1 | 0.9-1.0 | |

BasecRAWller Performance

The method can produce results equal or better in performance than other basecallers for nanopore sequencing while using substantially less computational resources to allow for the processing of data on a personal computer with similar or better accuracy than other basecallers for nanopore sequencing technology. Modifications to the neural network architecture and hyper-parameters can allow the method to outperform other basecalling methods. The improved performance can be achieved using an appropriate training data set to train the two neural networks and the application of appropriate segmentation techniques between the neural networks.

Advantages of basecalling using the systems and methods disclosed herein include the ability to process data in a streaming manner, keeping up with the increasing speed of raw sequencing data generated. The basecaller can have high accuracy. For example, the basecaller can have 70-80% accuracy or higher, for one dimensional (1D) or two dimensional (2D) basecalls, which is on par with other basecalling methods. To achieve the accuracy, a basecaller disclosed herein can implement various architectures and preprocessing. A larger sequencer from Oxford Naopore Technologies (Oxford, United Kingdom) can produce 12 Tb of data in 48 hours (up to 1.44 GBps). In some embodiments, a basecaller disclosed herein can have high accuracy, such as 85% or higher accuracy.

Figure 6A:
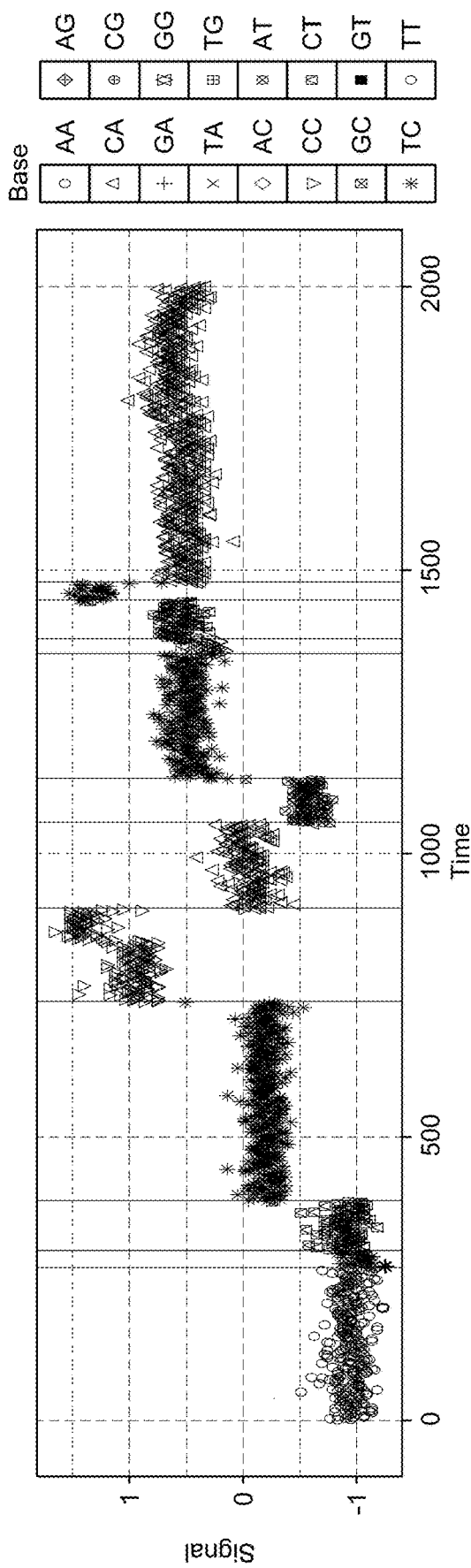
FIGS. 6A-6B shows example plots of sequence determination.
Figure 6A:
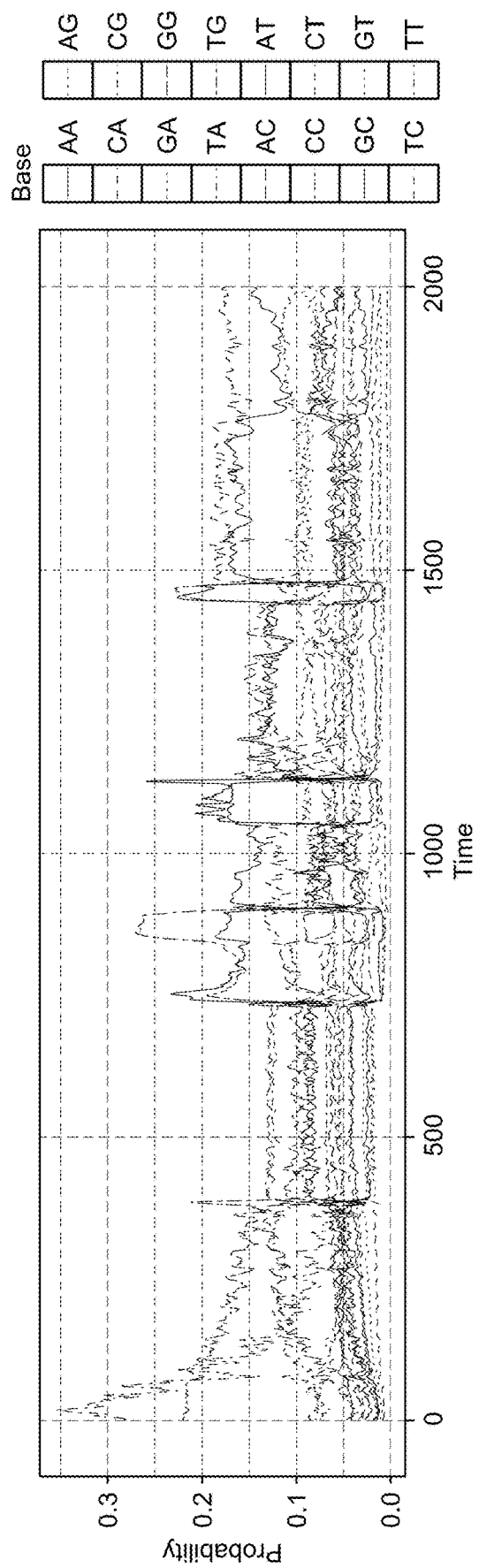
Figure 6B:
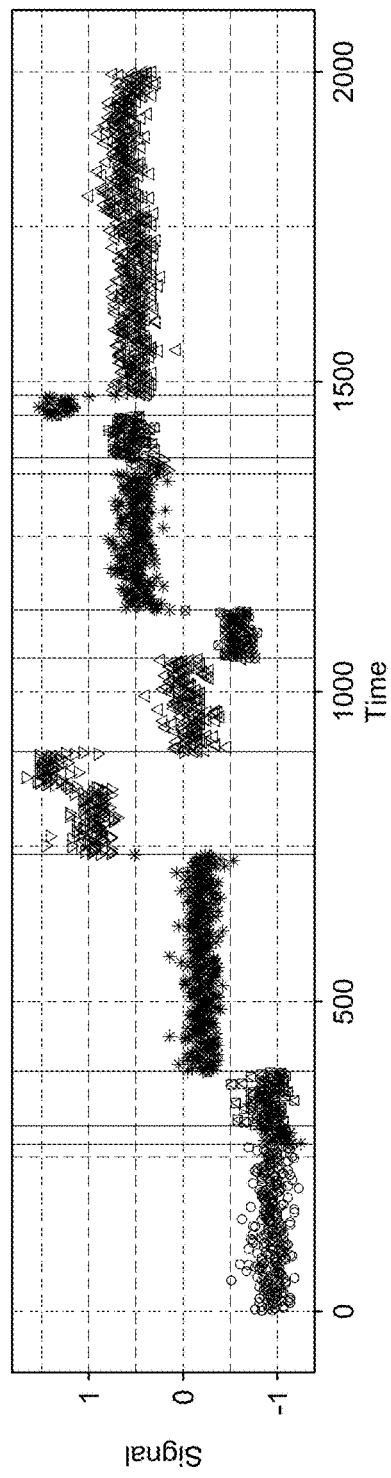
Figure 6B:
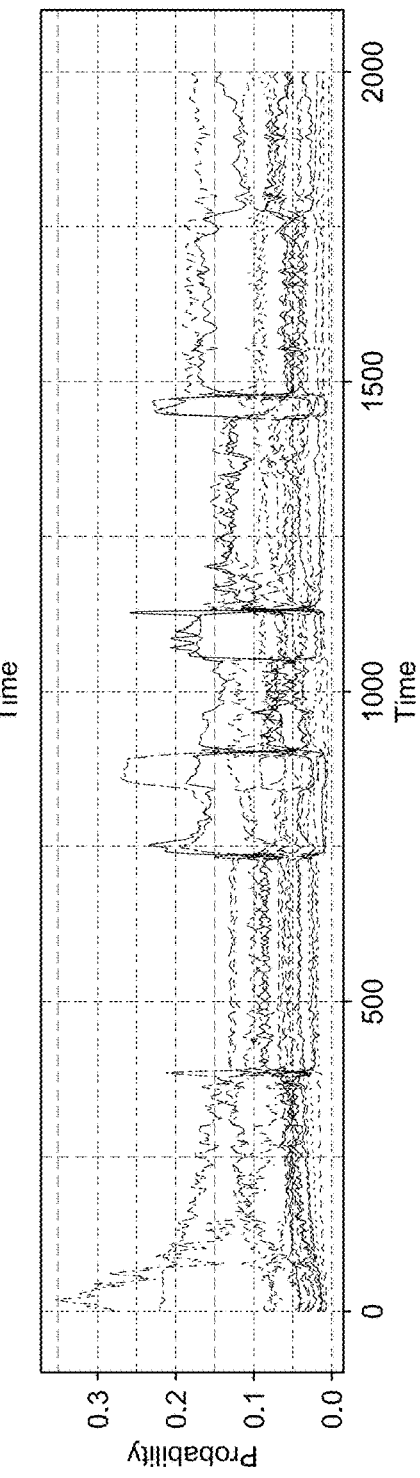
Figure 6B:
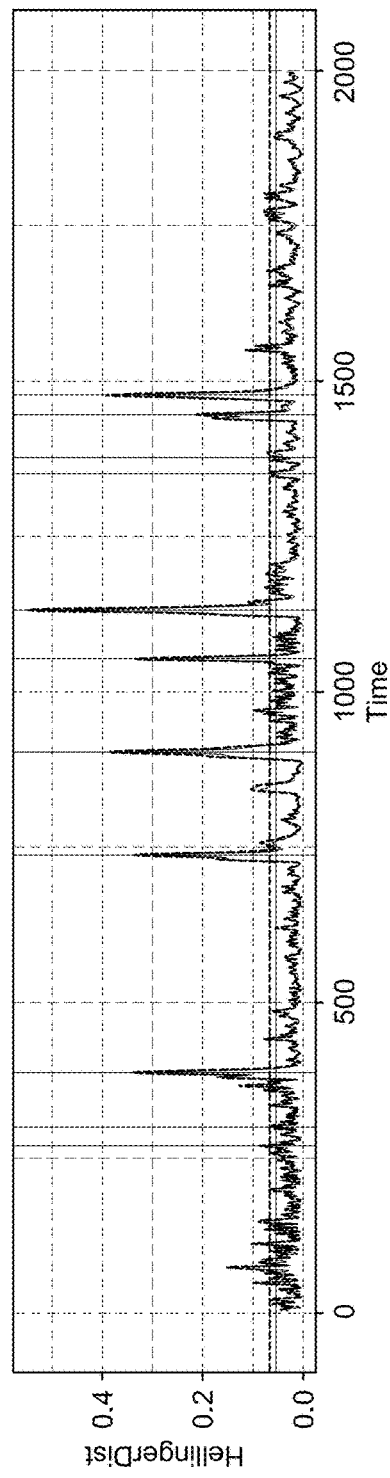

A basecaller implementing the basecRAWller method can have high accuracy, providing meaningful biological insight. A basecaller disclosed herein can have high adaptability. For example, the basecaller can be used to interrogate data in order to assess confidence and possible alterations. The basecaller can be used to investigate base alterations, such as methylation and acetylation, via one or more encoding layers. The basecaller can be used to provide quality control (QC) metrics for raw reads. In some embodiments, after segmentation and requiring concurrency between predicted events (with the Viterbi algorithm for example) accuracy can be higher. FIGS. 6A-6B show example plots of sequence determinations. Hellinger Distance offset and global threshold can be optimized for better performance.

Non-Standard Nucleotides

In some embodiments, the raw net can generate a start probability and a probability that the current observation is from a non-standard nucleotide (given appropriate training data) from raw nanopore sequencing data. The start probability and the probability that the current observation is from a non-standard nucleotide can be generated in a streaming fashion.

Just as nucleotide start positions can be predicted as the output of the raw net, so could any other variable of interest given an appropriate training data set. One of the outputs would be the presence of non-standard or modified nucleotides at any particular position within a read. This could be included within the basecRAWller process as a binary output from the raw net just as with base start position.

In addition to the presence of a non-standard nucleotide, prediction of the identity of that nucleotide can be of great value. As opposed to modeling this as a separate variable explicitly, an alternative approach with many benefits would be to take those positions identified as non-standard from the raw net output and feed some value associated with this nucleotide into a classifier, which would predict the identity of that non-standard nucleotide. Informative value input into this classifier can include layer encodings from the raw net associated with this predicted nucleotide. As the nucleotide is composed of several observations this could include any summary of the associated layer encodings across these observations associated with the predicted base including the mean, median, some specified quantile or middle (in time though the base) of the layer encoding values.

Once these layer encoding values are obtained for a predicted non-standard base, they can be fed into a random forest trained to predict the identity amongst some alphabet of non-standard nucleotides. A training data set can be constructed in order to observe each non-standard nucleotide within a range of sequence contexts, such as the 2-15 bases surrounding the non-standard base of interest. Thus as a final output such a basecRAWller process would produce the predicted sequence of any read, the position of any non-standard nucleotides and a prediction of the identity of those non-standard nucleotides.

This process can produce considerably more accurate than explicitly modeling the non-standard nucleotide identities directly mainly because as the alphabet of non-standard bases is increased it becomes increasingly difficult to predict a standard nucleotide within the space of many potential non-standard nucleotides. An alternative modeling based approach would be to pre-specify only a small portion of the non-standard alphabet, but this has the downside of the user not knowing the alphabet present within a particular sample and thus missing potentially very interesting biological findings. The binary prediction of non-standard bases followed by categorical prediction can produce optimal predictive results.

Execution Environment

Figure 7:
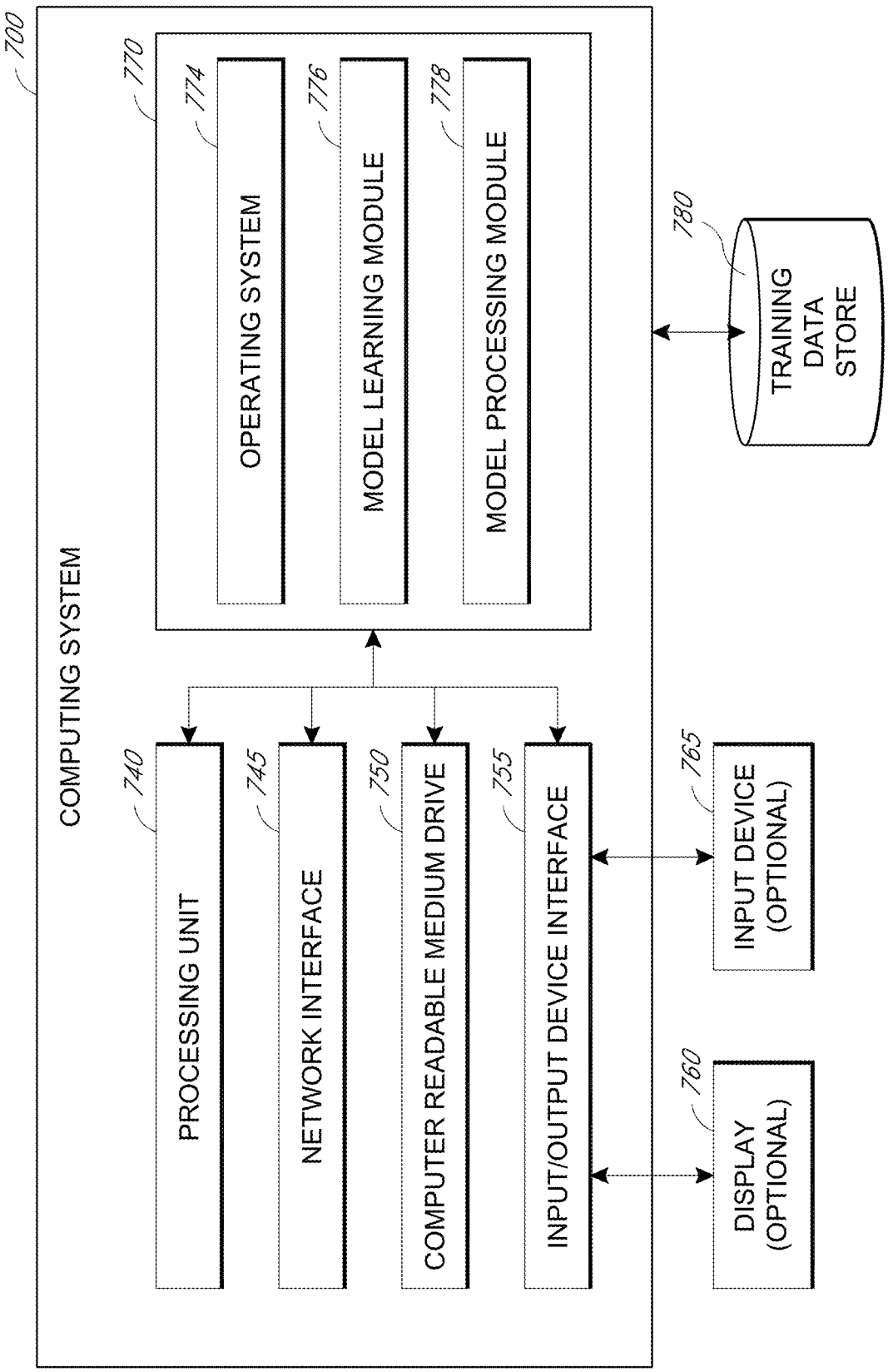
FIG. 7 depicts a general architecture of an example computing device configured to perform basecalling for the nanopore sequencing technology.

FIG. 7 depicts a general architecture of an example computing device 700 configured to learn a machine learning model and compute a prediction result using the model. The general architecture of the computing device 700 depicted in FIG. 7 includes an arrangement of computer hardware and software components. The computing device 700 may include many more (or fewer) elements than those shown in FIG. 7. It is not necessary, however, that all of these generally conventional elements be shown in order to provide an enabling disclosure. As illustrated, the computing device 700 includes a processing unit 740, a network interface 745, a computer readable medium drive 750, an input/output device interface 755, a display 760, and an input device 765, all of which may communicate with one another by way of a communication bus. The network interface 745 may provide connectivity to one or more networks or computing systems. The processing unit 740 may thus receive information and instructions from other computing systems or services via a network. The processing unit 740 may also communicate to and from memory 770 and further provide output information for an optional display 760 via the input/output device interface 755. The input/output device interface 755 may also accept input from the optional input device 765, such as a keyboard, mouse, digital pen, microphone, touch screen, gesture recognition system, voice recognition system, gamepad, accelerometer, gyroscope, or other input device.

The memory 770 may contain computer program instructions (grouped as modules or components in some embodiments) that the processing unit 740 executes in order to implement one or more embodiments. The memory 770 generally includes RAM, ROM and/or other persistent, auxiliary or non-transitory computer-readable media. The memory 770 may store an operating system 774 that provides computer program instructions for use by the processing unit 740 in the general administration and operation of the computing device 700. The memory 770 may further include computer program instructions and other information for implementing aspects of the present disclosure. For example, in one embodiment, the memory 770 includes a model learning module 776 that learns a machine learning model from training data. In another embodiment, the memory 770 includes a model processing module 778 that computes a prediction result (e.g., a basecalling) from raw nanopore sequencing data and a machine learning model, such as a machine learning model learned by the model learning module 776. In addition, memory 770 may include or communicate with training data store 780 and/or one or more other data stores that stores training data or raw nanopore sequencing data.

EXAMPLES

Some aspects of the embodiments discussed above are disclosed in further detail in the following examples, which are not in any way intended to limit the scope of the present disclosure.

Example 1 basecRAWller System

This example demonstrates the application of the basecRAWller system to two data sets from *E. coli* and human.

Method and Performance

Figure 8:
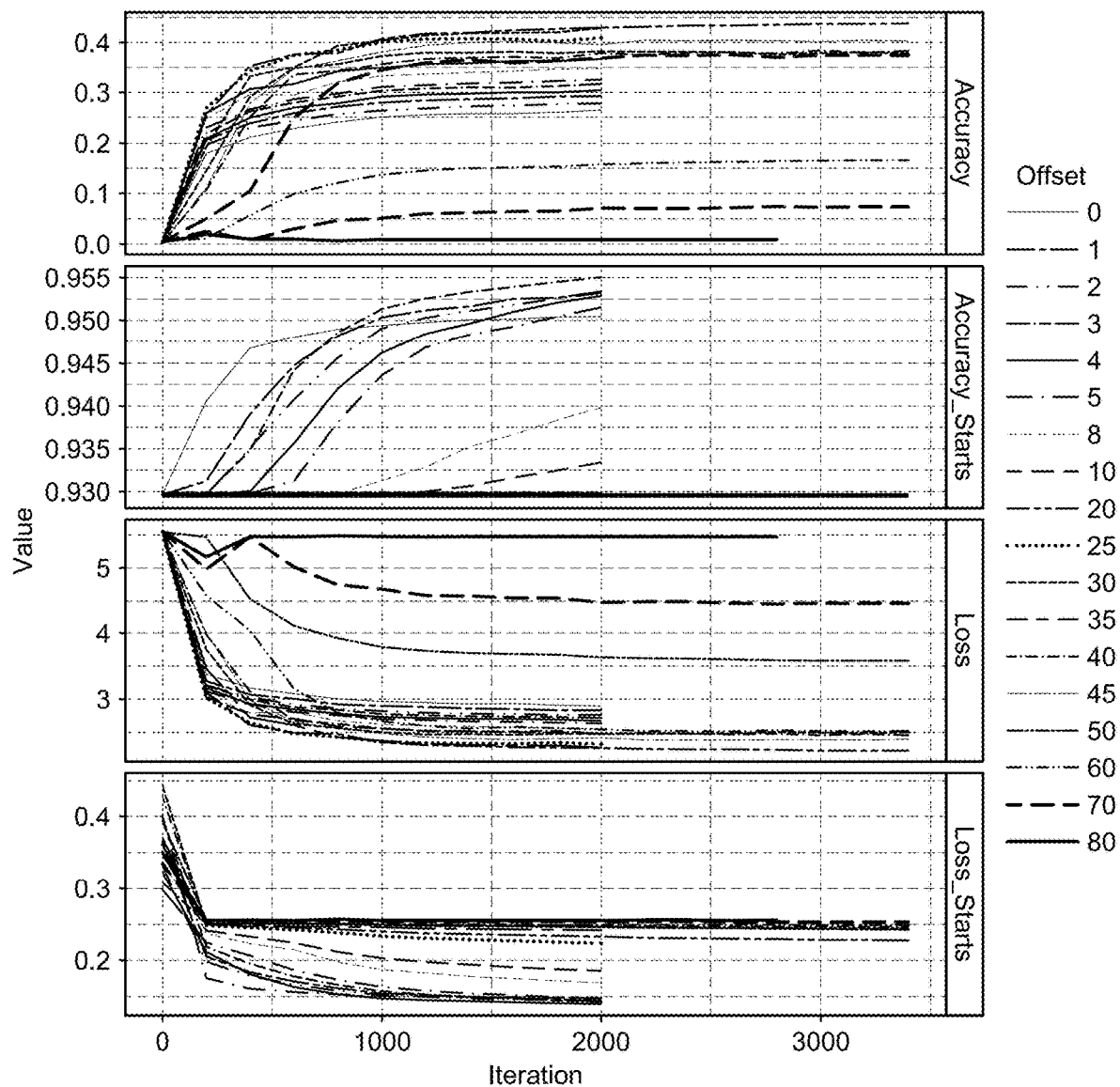
FIG. 8 shows raw net fitting performance over iterations for a range of the offset parameter. The final chosen value for trained nets was 33.

The basecRAWller process was based on a pair of recurrent neural networks, referred to as the raw and fine-tune nets (FIGS. 4 and 5A-5C). This network took in scaled DAC values and outputs multinomial logit predictions for each 4-mer associated with each observation. The raw net composed of several stacked long short term memory (LSTM) units (e.g., Hochreiter, S. et al. Long short-term memory. Neural Comput 9, 1735-1780 (1997), the content of which is hereby incorporated by reference in its entirety) followed by several fully connected layers. This network took in scaled DAC values and outputs multinomial logit predictions for each 4-mer associated with each observation. These predictions were made at a delay of 33 raw observations (less than 1/100th of a second in sequencing time), which allowed the network to take in signal at a brief lag past an observation before predicting the associated sequence allowing for modulation of the predicted sequence (FIG. 8). This network simultaneously output the probability that each observation corresponds to the beginning of a new base. A segmentation process was then applied to split the continuous sequence predictions into discrete events. The 4-mer predictions, averaged over each event were then be passed to the fine-tune net to produce final sequence predictions, including small inserted bases (2 bases per event) and event deletion. These predictions were made at a delay of two base pairs (approximately 0.005 seconds) and the output of this neural network comprised the final predicted sequence from the basecRAWller process.

Figure 9:
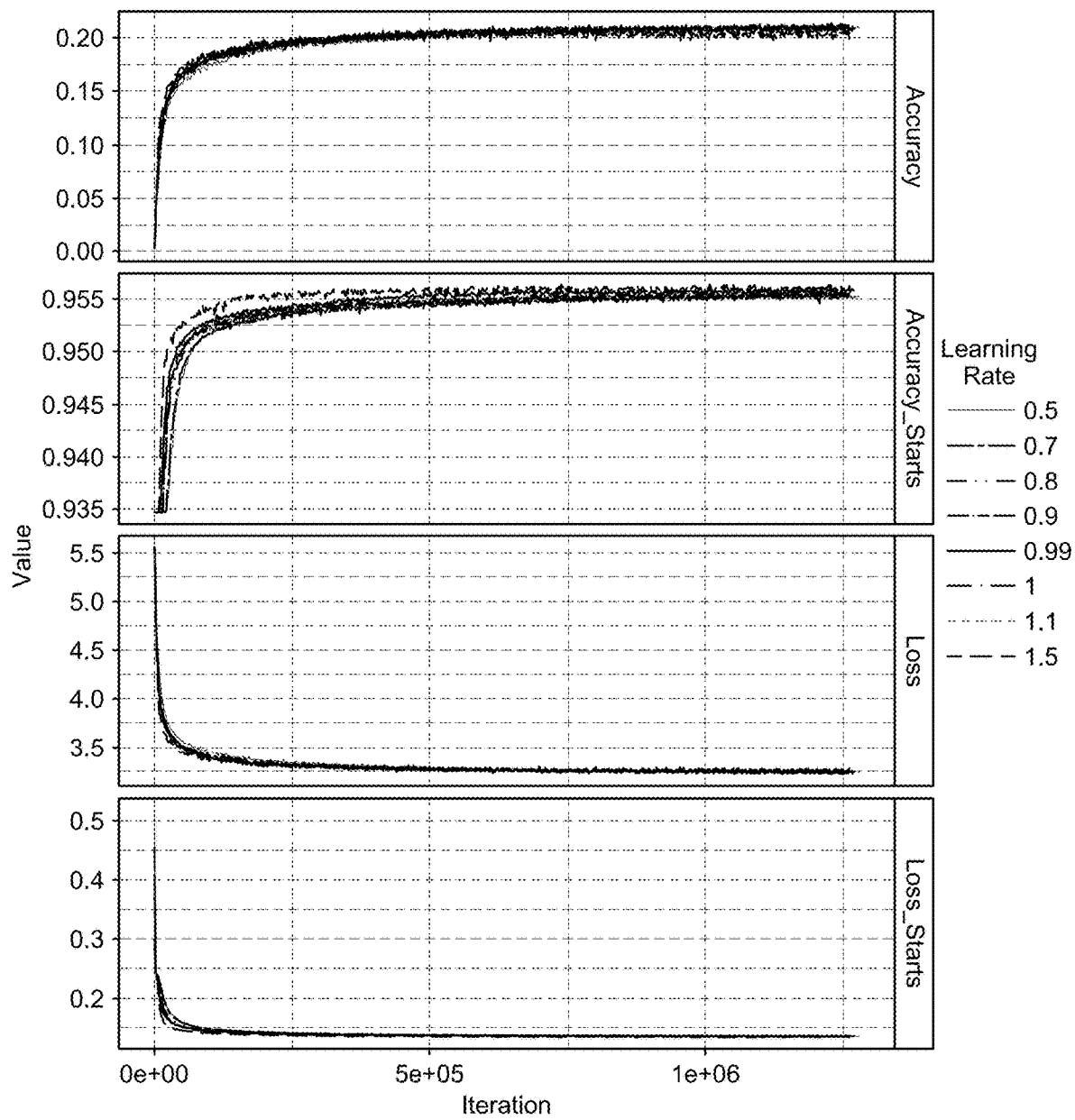
FIG. 9 shows that the learning rate had a relative small effect on the raw net accuracy.
Figure 10:
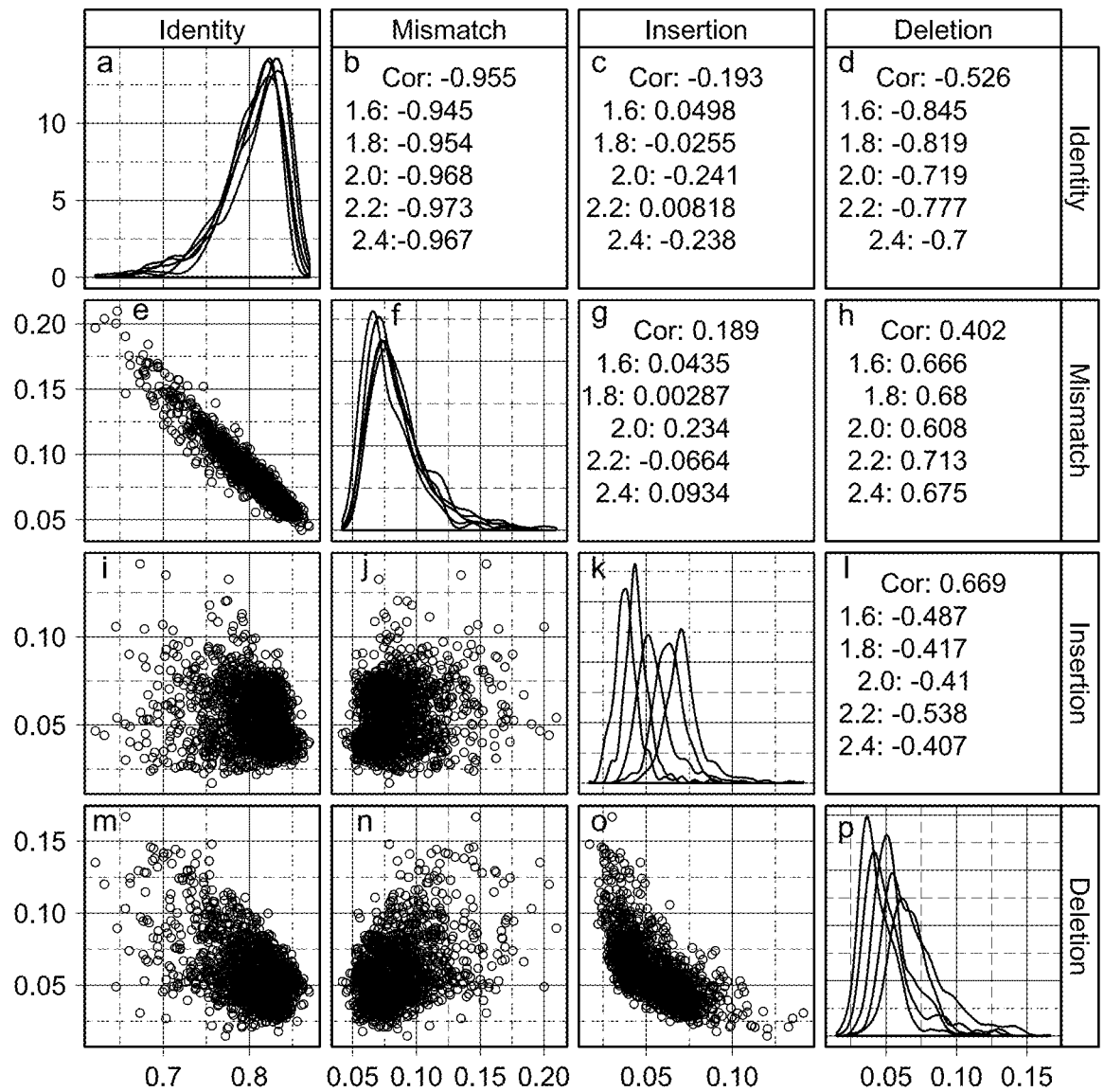
FIG. 10 shows comparison of mapping statistics for over 5 models trained with the same parameters except for the insertion penalty training parameter. Models show similar percent identity and percent mismatch while showing a range of insertion and deletion rates.

Models were trained based on each version of the nanopore technology or sample type and applied where applicable (including translocation speed, native versus amplified, ratchet protein and other workflow difference). The learning rate had a relative small effect on the raw net accuracy (FIG. 9). Particular parameters were tuned to alter error profiles. For example, the insertion penalty training parameter produced basecRAWller models with a range of insertion to deletion ratios (FIG. 10). The human data trained model was the default provided with by the basecRAWller software.

FIG. 10 shows that insertion to deletion rations of the basecRAWller process can be tune-able. For example, penalty can be applied to inserted bases and deleted events in training (FIG. 10, panel a). There can be one categorical output for deleted events and $4^2=16$ categories for one inserted base. Similar percent identity can be maintained. The basecRAWller process can be based on a model that allows for variable insertion to deletion ratios (FIG. 10, panels k, p).

The basecRAWller process was applied to two data sets from: E. coli (two control samples from Marcus H Stoiber, et al., De novo Identification of DNA Modifications Enabled by Genome-Guided Nanopore Signal Processing. bioArxiv 094672 (2016), the content of which is hereby incorporated by reference in its entirety) and Human (Nanopore WGS Consortium, NA12878 from Miten Jain, S. K., et al. Nanopore sequencing and assembly of a human genome with ultra-long reads. bioaRxiv 128835 (2017), the content of which is hereby incorproated by reference in its entirety). These samples were processed with entirely different procedures: different library preparation workflow (FLOMIN-105 vs. 1D ligation), translocation speed (250 bps vs 450 bps), read types (1D vs 2D) and flow cell (R9 vs. R9.4) so these data sets represent divergent nanopore data. Performance of neural networks trained and tested on either data set (FIG. 11) revealed that a basecRAWller model trained on the human data set can be more robust across the two diverse data production pipelines, most likely due to the DNA translocation speed which drastically changes the nature of the raw data. The basecRAWller model trained on the E. coli data set was robust to an independent held out E. coli replicate (different library preparation and flowcell; same lab).

Initial comparisons to basecalls from Oxford Nanopore Technology's albacore basecaller showed that the basecRAWller process was performing much faster, but with lower accuracy of basecalls (FIG. 11), paying a penalty for the advantage of streaming performance. However, improvements in speed versus accuracy are likely to improve accuracy that will come with additional training and basecRAWller neural network hyper-parameter selection. Both of these tasks can be enabled by the basecRAWller system. All hyper-parameter testing was completed using the E. coli data set, so increased performance should be achievable in the human data set with additional hyper-parameter searching.

Figure 11:
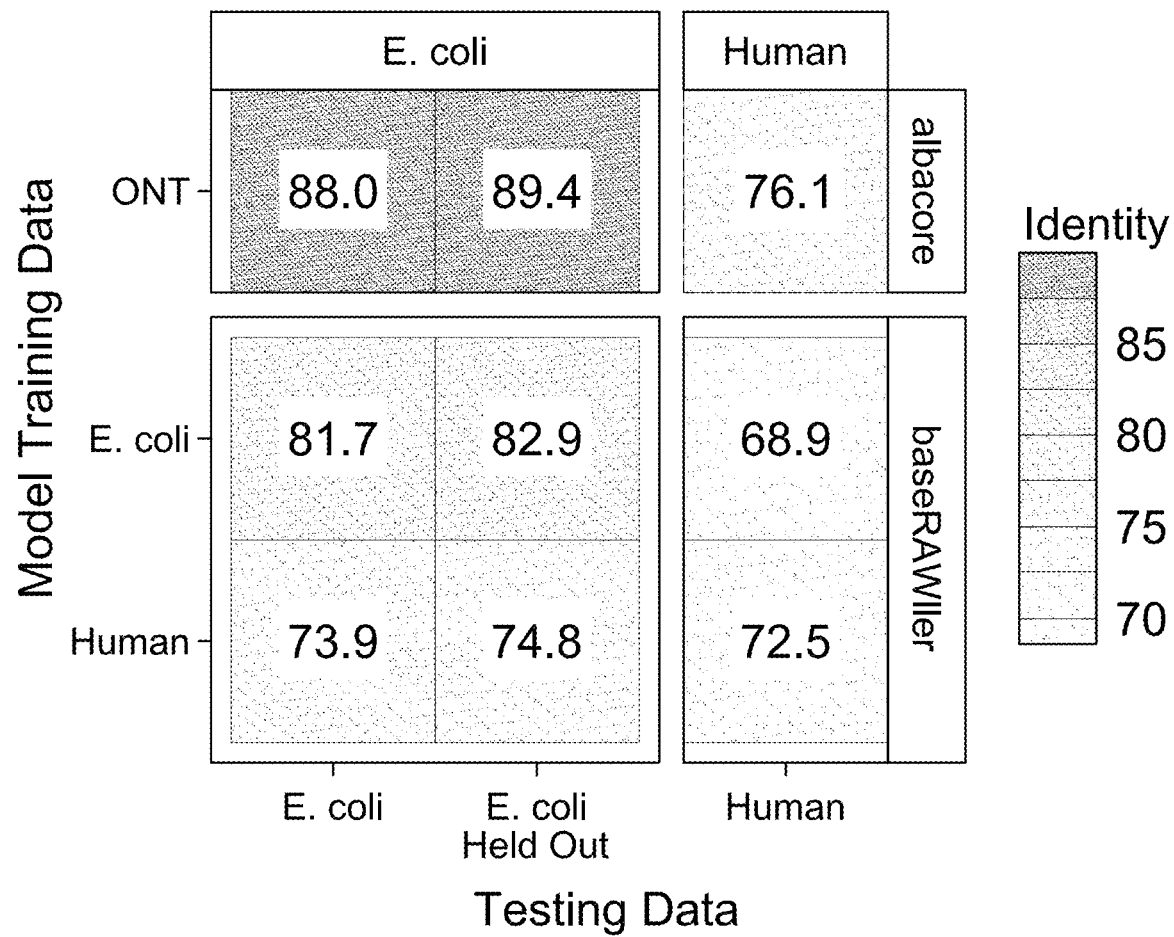
FIG. 11 shows performance of the BasecRAWller process. Data used for testing is shown on the x-axis, and data used for testing is shown on the y-axis. Oxford Nanopore Technologies (ONT) basecaller albacore in the top panel is compared to the basecRAWller trained models.

As shown in FIG. 11, two testing data sets were used: E. coli, R9, amplified, 250 base pairs per second, 2D (from nanoraw); and human, R9.4, native, 450 base pairs per second, 1D (from nanopore WGS Consortium). Hyper-parameter optimization was performed on the E. coli data set. In some implementations, there can be a tradeoff between streaming and accuracy.

Raw Net

Once normalized DAC values were computed, they were fed into a recurrent neural network (RNN), specifically a number of unidirectional (in the direction of sequencing time) long short term memory (LSTM) layers followed by one or more fully connected layer. FIGS. 5A-5B show an exemplary architecture of this first neural network (referred to herein as the raw net). This network took as input a single scaled DAC value and returned a vector of logits (transformed probability values) that any oligonucleotide is represented by a DAC value, as well a "memory" that was passed on to the next observation along with the next scaled DAC value. In parallel, the raw net output a logit value that this position was the beginning of a new base to be potentially used in the segmentation step. It should be realized that this network can be constructed with any number of LSTM layers, each with any number of output units (entered as a parameter during training). The oligonucleotide to predict was also variable by specifying the number of bases before and after the current base to be included. For all analyses presented in this example, a three layer network with 75, 100 and 50 output nodes and output 4-mers was used. The third layer was added after training the two-layer network in order to more quickly identify appropriate parameters for the first two LSTM layers. The basecRAWller software provided this functionality.

Constructing appropriate training data sets and setting training parameters can affect the success of this system. Starting with basecalled reads by the Oxford Nanopore Technologies (ONT) platform, training data was constructed by applying the nanoraw software package (Marcus H Stoiber, Jet al, De novo Identification of DNA Modifications Enabled by Genome-Guided Nanopore Signal Processing. bioArxiv 094672 (2016), the content is hereby incorporated by reference in its entirety) genome_resquiggle process. This process resolved error prone basecalls with a genomic alignment so that raw signal was assigned to potentially perfect basecalls from a known source (here E. coli or human). For the raw net this allowed the assignment of each raw DAC value with the true oligonucleotide centered on that position and defined by a number of positions before and after the current position. The nanoraw software package can implement genome re-squiggle algorithm and statistical testing to identify modified nucleotides. The software package can generate reproducible results across laboratories.

To construct training and testing data sets, nanopore reads were provided (7,500 are provided for both presented trained models). For each read a random starting position between the start and middle of a read is selected. This was in order to avoid any over-fitting to the start of reads that would all be presented at once to be trained in the initial iterations of each epoch. Then the reads longer than the 50th percentile of read lengths were included in the training data (3,740 reads included for fitted models; this value showed good robustness with held out test data with reasonable computational efficiency). This was so that a training epoch (all provided data) was long enough to allow inclusion of enough variety and amount of data. These reads, each starting at their randomly selected position, were combined into a matrix with the length of the 50th percentile read length (i.e. the shortest read included in the training data set). Additionally, another vector was provided with the true start positions for each base in each read to train the base start raw net output. This procedure was encoded in the prep_raw_net command in the basecRAWller system software package.

In order to more accurately predict base sequence from raw signal, the raw net was trained to predict the sequence at delay. For both networks presented in this example, this delay was set to 33 observations (less than 1/100th of a second in sequencing time), which was chosen after testing several values in this range (FIG. 8). This allowed the network to take in the signal well past a given observation, which modulated the predicted sequence, before producing a final sequence prediction. Significantly improved prediction was possible with appropriate parameter testing for the newer 450 bp/sec sequencing model.

In addition to these high impact parameters (and training hyper-parameters discussed below, "neural network training" section) there were several parameters specific to the raw net training. Specifically, the following parameters were tested for effect on model accuracy as well as computational training time. The number of observations included in each training iteration had a reasonable effect on the final output with values greater than greater than 300 showing reasonable comparative results. The value used for both trained models was 500 as greater values were again prohibitively computationally expensive. The neural network learning rate was set to 1.0 for presented trained models, with values between 0.5 and 1.5 showing reasonable results. In order to stabilize the model as it got closer to a global minimum the learning rate is halved every 500 observations. This value showed reasonable results in the range of 200-10000 observations. The momentum parameter was used by the gradient ascent process to maintain the direction of fitting from iteration to iteration and was set to 0.9 for both models presented here. Values between 0.85 and 0.99 showed reasonable results. Given the outputs of sequence probabilities and base start positions, a parameter was provided to control the proportion of the loss attributed to the base starts cross-entropy loss and the proportion attributed to the oligonucleotide sequence cross-entropy loss. This parameter is set to 1.1 (10% more weight attributed to start position loss) for both fitted models. Values between 0.8 and 1.5 showed reasonable results. In order to allow the base start proportions to "ramp up" before and "ramp down" after a true base starts then positions within a range around true base starts are masked, their loss values were set to 0. For both fitted models two observations around the true starts were masked, with reasonable values being between 0 and 3. During training the probability that any connection between two nodes was included was available as a parameter to the basecRAWller model, but this parameter showed little improvement in the fitted model, so all connections were included during training (parameter value 1.0). The basecRAWller help command included recommended ranges for all parameters obtained by training over a range of values from more than 200,000 hours of compute time.

The raw net was also designed to output events back into the raw files thus allowing iterative training of basecRAWller models (i.e. preparing training data for a basecRAWller model from a basecRAWller trained basecaller). Limited success was found with this procedure thus far.

In addition, the capacity to restore the training of the raw net with a new LSTM layer has been provided by the basecRAWller software. This restoration process restored the trained parameter values to the LSTM layers, added a new LSTM layer with a specified node size and fully connected layer that may not be restored due to the new structure connecting to a new LSTM layer. This procedure was employed for both trained raw nets provided in this example.

Segmentation

The raw net produces, for each raw observation, a vector of logits representing the probability that this observation was derived from each distinct oligonucleotides along with a prediction that this position was the start of a new base. For the *E. coli* basecRAWller model presented in this example, the raw net base start predictions were sued. Two other measures (running Hellinger distance and entropy difference) performed better on the human trained model. Specifically, the entropy difference between logit vectors at a lag of two observations up and downstream of the current observation was used for downstream segmentation.

For any of these measures, peaks were identified. Peaks were required to be four observations apart for all models presented in this example, but this value was a parameter for tuning in the basecRAWller software. To save computational time during training only the first 100,000 observations (25 seconds) were used for splitting metric computations. From these valid peak locations, a global cutoff value was used. All peaks with value above this threshold were used as the defining points for segmentation into events.

A command in the basecRAWller software to "analyze_splitting" was used in order to identify an optimal cutoff for any trained networks. This optimal value was determined by analyzing some number of reads and choosing the global cutoff value which minimized the difference between the true number of splits for each read and the number identified given a global peak, cutoff value. This value and the splitting criterion were stored within the model for future training or final basecalling applications.

The alternative measures, Hellinger distance and entropy difference, were computed from the matrix of oligonucleotide logits at some fixed offset before and after each observation. Hellinger distance was a natural measure of the distance between two multinomial distributions, which was the exact realm we find when looking for segmentation locations. It was natural for the probability distribution to shift considerably centered at a transition between true bases. Similarly entropy was a measure of a statistical distribution and shifted in entropy through time again indicated a shift from one base to another. Both of these values were provided as options for tuning the basecRAWller basecaller process, or (the default during training) all three measures were computed and whichever measure was found to identify the number of split locations most accurately from a global cutoff was chosen dynamically. In some embodiments, upon selection of an alternative measure the fine-tune net may need to be re-trained.

After segmentation positions were identified, a matrix was prepared in order to train the fine-tune net. This matrix had dimensions of the number of identified segments by the number of oligonucleotides (predicted from the first net). For each segment the probability distribution was averaged over the identified segments. This vector represented the probability that this segment belonged to any particular oligonucleotide. This vector of probabilities was computed for each segmentation point identified and passed to the fine-tune net for training or dynamically for basecalling.

Fine-Tune Neural Network

After raw net processing, segmentation and distribution averaging a second neural network was applied to fine-tune the predicted bases from the raw net. The structure of the fine-tune net was identical to the raw net with some number of LSTM layers followed by one or more fully connected layers that output probability values. FIG. 5C shows the structure of the raw net. The difference was that each observation taken in by the fine-tune net was a vector of logits for each possible oligonucleotide instead of a single normalized DAC value and the output is zero, one, two or three bases represented by this segment. For the analysis presented here two LSTM layers with 200 and 75 nodes were used. The output of the fine-tune net was the logit values for between 0 and some length of oligonucleotide that represented the bases to assign to the current segment. The 0-length state indicated that the current segment should be deleted and should have been joined with the previous segment. The 1-mer state indicated that this segment was correctly assigned a single base and specifies the specific base for that segment. The 2-mer and greater states indicated that the current segment represents more than one base (was under segmented). The maximal number of inserted bases for all analyses presented was set to two. This can be a parameter for tuning future basecRAWller models available in the basecRAWller software.

As with the raw net, the fine-tune net was trained to predict bases at a delay in order to take in values past the current base allowing for modulation of the sequence predictions given predictions slightly in the future. For both models presented in this example, this offset was set to 2 segments, representing approximately 18 observations or again less than 1/100th of a second. This parameter had a smaller, but discernible effect than the raw offset parameter.

The construction of the training data for the fine-tune net can be important as there was a discordance between the identified segmentation from the raw net and the ideally true segments identified by the nanoraw genome_resquiggle assignments. The sequence assigned to each segment for training was determined so that the last base was the first base within the segment of interest as long as the true segment position fell within 3 observations of the raw net segmentation position (this value was tune-able with a parameter to the basecRAWller training pipeline). If there was no such true segment position then the segment was assigned the last true base from the previous raw net determined segment, as long as it was not assigned to the previous segment. If this was the case then the segment of interest was assigned no bases (a deleted event). If there are additional true bases included within the previous segment of interest these bases (up to a limit; 2 for fitted models) were included in the segment of interest for training (inserted bases). Given this training setup the output of the fine-tune net represented the final sequence for a read provided in a completely streaming fashion.

Given this output type for the fine-tune net the deletion categories were prone to over-prediction. Any deleted base was represented by a single deletion category, while a single inserted base was represented by 16 output categories (for all combinations of the assigned base and the inserted base). Thus a parameter was provided to maintain equal (or tuneable) insertion to deletion rates. In order to achieve approximately equal insertion and deletion rate this parameter was set to 2.0 (single base insertion categories loss values were inflated by $2.0^{\wedge}2-8$ times compared to deletion categories; similarly two base insertion category loss values were inflated by $2.0^{\wedge}3-16$ times). Tuning this parameter allowed basecRAWller models with different insertion to deletion ratios, which may be of value in particular situations.

As with the raw net there were several general neural network training parameters which needed to be set. The number of observations included in fine-tune net training was set to 90 for models presented in the example (with values around 100 showing reasonable results). The learning rate halving parameter was set to 3,000 for the fine-tune net. Additional, parameters were set very similarly to the raw net: learning rate is set to 0.9 and momentum was set to 0.9.

Runtime Performance

In some implementations, basecRAWller was computationally efficient, allowing basecalling at speeds faster than current nanopore instrument measurement speeds. For example, in one embodiment, BasecRAWller neural network models can be based on the tensorflow python software interface (Martín Abadi, et al. TensorFlow: Large-scale machine learning on heterogeneous distributed systems, (2015), download.tensorflow.org/paper/whitepaper2015.pdf, the content of which is hereby incorporated by reference in its entirety). On a single Intel Xeon E5-2698 v3 (2.3 GHZ) processor, read processing speed of greater than 8000 observations per second was achieved, twice as fast as current sequencer data collection speeds. Processing was concentrated on the raw net, which consumed ~90% of the processing time, while the segmentation process took a negligible amount of time and the fine-tune net consumes the remaining 10% of processing time. Some parameters were sensitive to processing time. For example, the number and size of LSTM layers used in the raw net had a large effect on the final processing speed of a basecRAWller model.

DAC Signal Normalization

Figures 12A, 12B:
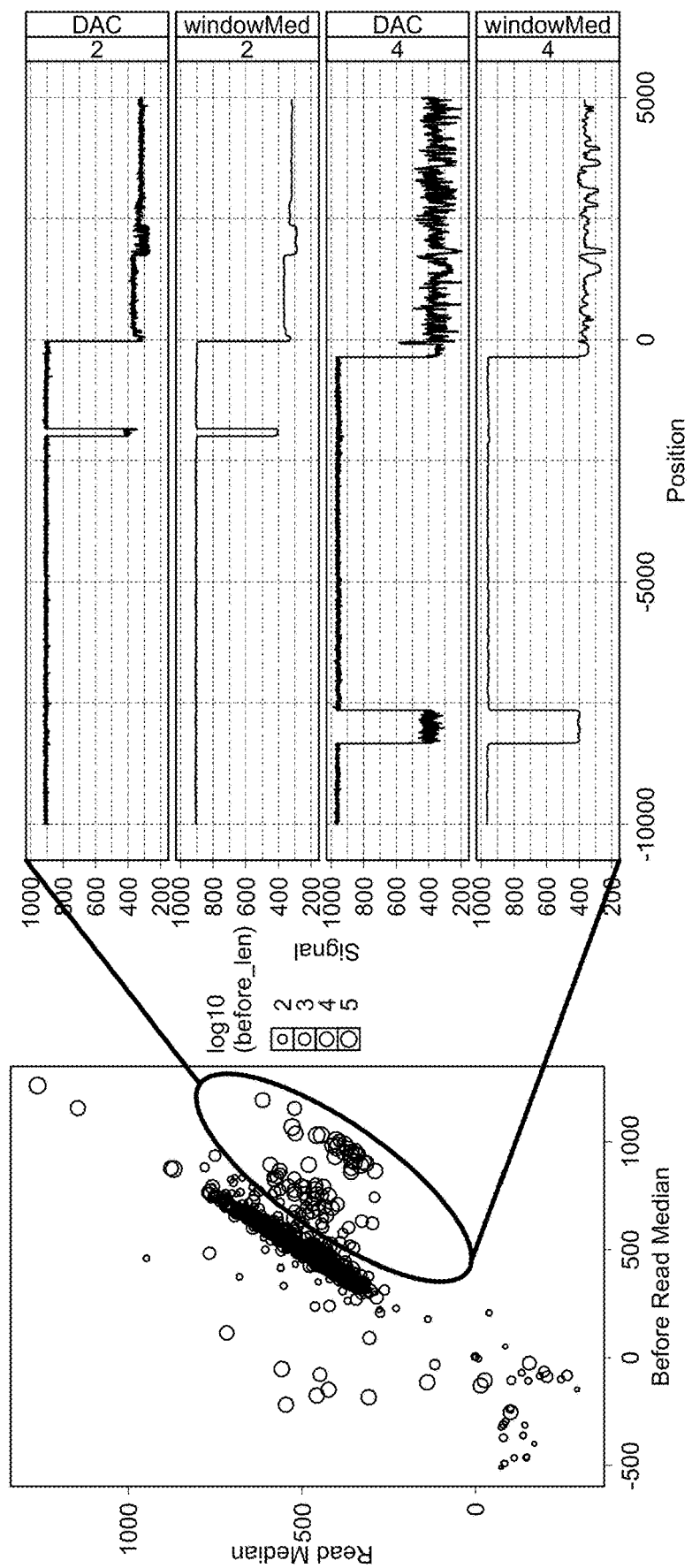
FIGS. 12A-12B shows the effect of enabling full streaming pipeline by using median of a nanopore signal from before the beginning of a read.
Figure 13A:
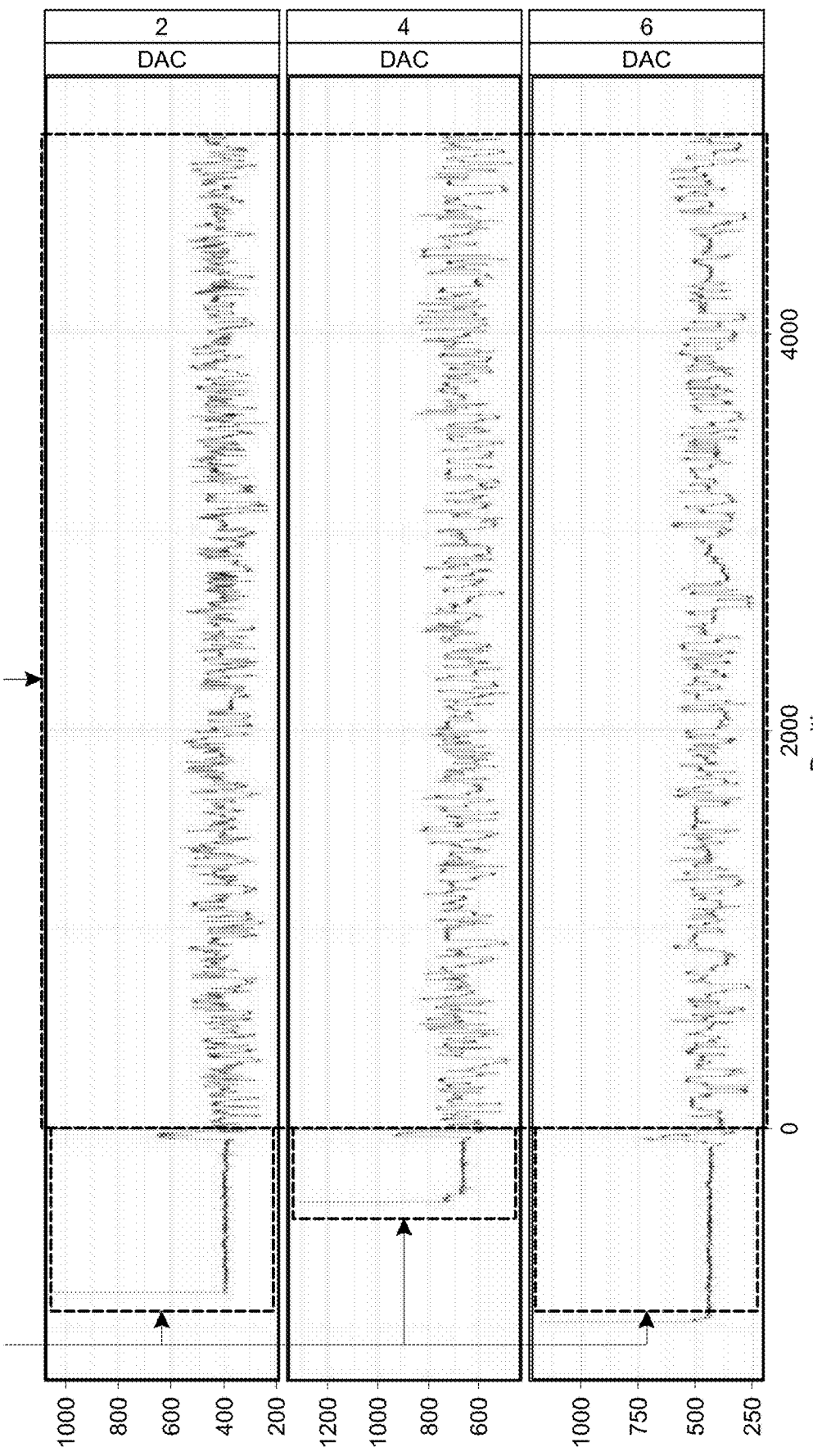
FIGS. 13A-13C show another illustration of streaming signal normalization.
Figure 13B:
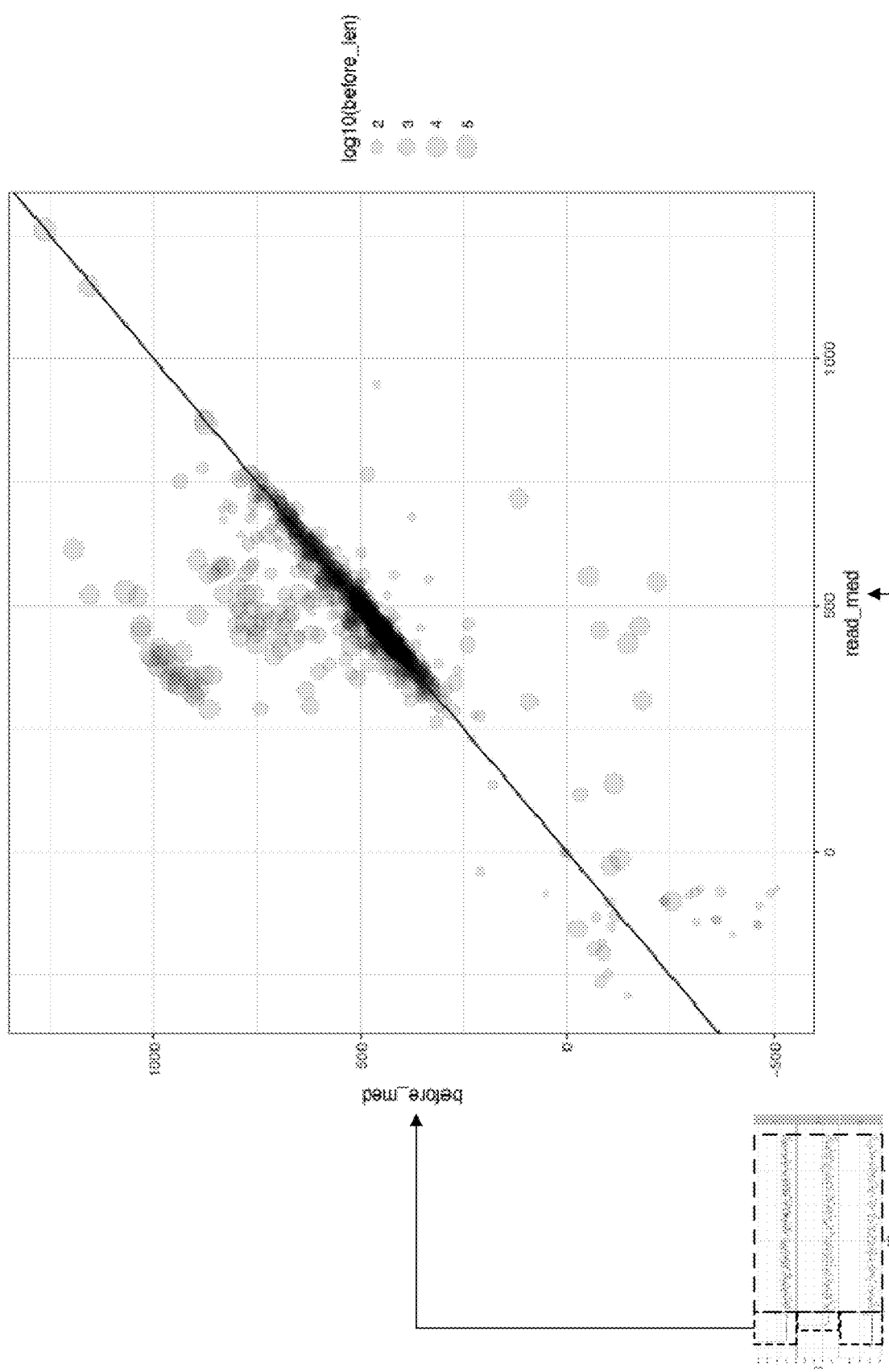
Figure 13C:
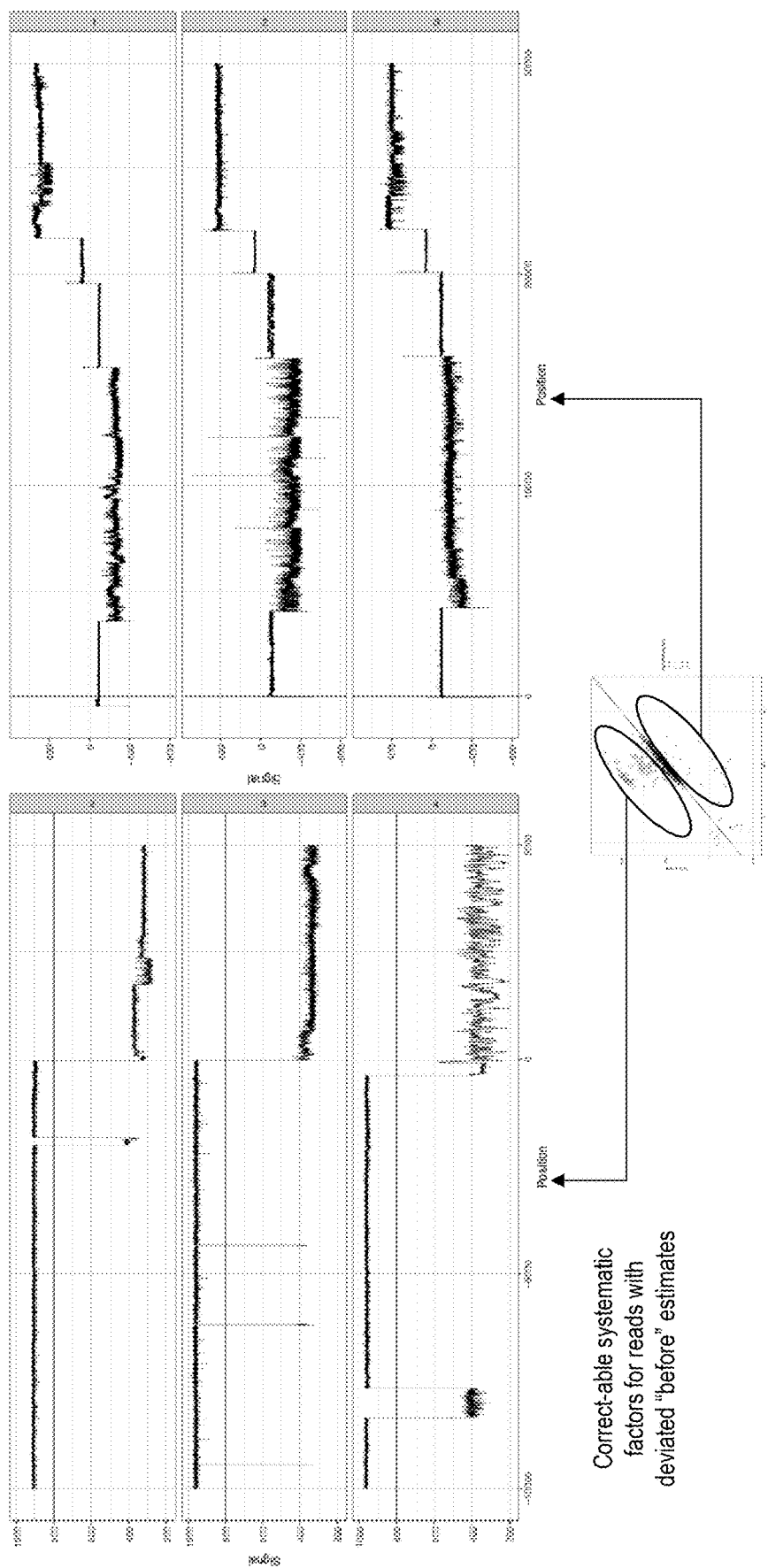

The basecRAWller process began from a contiguous section of nanopore data acquisition (DAC) values that corresponded to a continuous strand of DNA. As there was drift in the relative levels of DAC values, the first step in the basecRAWller process was to normalize the DAC values. In the embodiment of a basecRAWller in this example, median normalization was used as reported in Marcus H Stoiber, et al., De novo Identification of DNA Modifications Enabled by Genome-Guided Nanopore Signal Processing. bioArxiv 094672 (2016), the content of which is hereby incorporated by reference in its entirety. This normalization procedure required the full signal (or some minimal proportion) and would thus inhibit the full streaming capabilities. To alleviate this roadblock the signal immediately upstream of the read start was investigated. This signal level was found to correlate very well with the median signal within the read (correlation: 0.76), and could thus be used as a surrogate for streaming applications (FIG. 12A). This analysis used a simple rolling window median of DAC values followed by application of a global cutoff criterion to identify open pore positions. This correlation could be made substantially stronger with more accurate identification of occupied pore locations (FIG. 12B). With this modification, the entire basecRAWller pipeline comprised a fully streaming nanopore basecalling application. FIGS. 13A-13C shows another illustration of streaming signal normalization.

In one embodiment, the basecRAWller pipeline includes the capacity to detect covalently modified bases. This detection may be in real-time. This embodiment may add the potential to improve cancer and toxicological research along with foundational and environmental biology. Just as base start positions are an output of the raw net, modified bases can be identified without combinatorial expansion in the space of 4-mers. The basecRAWller software may reduce barriers to entry to help develop diverse nanopore basecalling systems and methods, and, ultimately, to explore the space of extant DNA modifications throughout the biosciences.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for nanopore sequencing basecalling, comprising:
- a membrane defining a pore wherethrough a biomolecule is threaded to generate raw nanopore sequencing data;
- a computer-readable memory storing executable instructions; and
- one or more hardware-based processors programmed by the executable instructions to perform steps comprising:
  - receiving the raw nanopore sequencing data comprising a plurality of continuous data acquisition (DAC) values corresponding to the biomolecule;
  - normalizing the raw nanopore sequencing data to generate normalized nanopore sequencing data comprising a plurality of normalized DAC values in a streaming manner;
  - generating a vector of transformed probability values using a first neural network (NN) and a normalized DAC value of the plurality of normalized DAC values, wherein the first NN comprises a first recurrent neural network (RNN), wherein the first RNN comprises a first plurality of long short term memory (LSTM) layers, wherein a LSTM layer of the first plurality of LSTM layers comprises a first unidirectional LSTM layer, wherein the first unidirectional LSTM is followed by one or more fully connected layers; and
  - determining a base in the biomolecule using a second NN and the generated vector of transformed probability vectors, wherein the second NN comprises a second RNN, wherein the second RNN comprises a second plurality of LSTM layers, and wherein a LSTM layer of the second plurality of LSTM layers comprises a second unidirectional LSTM layer, wherein the second unidirectional LSTM is followed by one or more fully connected layers.

2. The system of claim 1,
wherein a position of the vector corresponds to an oligonucleotide, and
wherein a transformed probability value, of the transformed probability values of the vector, at the position of the vector comprises a probability of the oligonucleotide being represented by the DAC value.

3. The system of claim 2, wherein the oligonucleotide comprises a 4-base oligonucleotide.

4. The system of claim 1, wherein normalizing the raw nanopore sequencing data comprises using median normalization of the plurality of DAC values to generate the normalized nanopore sequencing data.

5. The system of claim 1,
wherein a DAC value of the plurality of DAC values corresponds to a read start DAC value,
wherein the raw nanopore sequencing data comprises a second plurality of DAC values upstream of the read start DAC value, and
wherein normalizing the raw nanopore sequencing data comprises using one or more second DAC values of the second plurality of DAC values upstream of the read start DAC value to generate the normalized nanopore sequencing data.

6. The system of claim 1, wherein the first plurality of LSTM layers comprises three LSTM layers.

7. The system of claim 6, wherein the three LSTM layers each comprise 75, 100, and 50 nodes, respectively.

8. The system of claim 1, wherein the first plurality of LSTM layers is followed by one or more fully connected layers.

9. The system of claim 1, wherein the method further comprises:
generating a second vector of transformed probability values using the first NN, a second normalized DAC value of the plurality of normalized DAC values, and a memory value.

10. The system of claim 1, wherein the vector of transformed probability values comprises a vector of logits of transformed probability values.

11. The system of claim 1, wherein generating the vector of transformed probability values comprises: generating, using the first NN and the normalized DAC value of the plurality of normalized DAC values, the vector of transformed probability values and a memory value.

12. The system of claim 1, wherein generating the vector of transformed probability values comprises: generating, using the first NN and the normalized DAC value of the plurality of normalized DAC values, the vector of transformed probability values at a delay.

13. The system of claim 12, wherein the delay comprises a duration corresponding to a number of DAC values of the plurality of DAC values, and wherein the number of DAC values of the plurality of DAC values comprises 33 DAC values of the plurality of DAC values.

14. The system of claim 1, wherein the method further comprises:
segmenting the plurality of normalized DAC values into a plurality of discrete events.

15. The system of claim 1, wherein the base corresponds to two base insertions or single deletion.

16. The system of claim 1, wherein the base comprises a non-standard base.

17. The system of claim 16, wherein the method further comprises:
determining the non-standard base using a classifier.

18. The system of claim 17, wherein the classifier comprises a random forest.

19. The system of claim 17, wherein determining the non-standard base using the classifier comprises using DAC values of the plurality of DAC values within an event.

20. The system of claim 1, further comprising training the first NN and the second NN, wherein the training the first NN comprises training the first LSTM layer of the first plurality of LSTM layers, followed by training the second LSTM layer of the first plurality of LSTM layers, and the training the second NN comprises training the first LSTM layer of the second plurality of LSTM layers, followed by training the second LSTM layer of the second plurality of LSTM layers, wherein the training the first NN and the second NN further comprises obtaining a training data set using a HMM-based basecaller, wherein obtaining the training data set comprises mapping a long read and aligning a raw electric current signal through a called event to a genome.

21. The system of claim 20, wherein the training data set is based on a cDNA.

22. The system of claim 20, wherein the training data set is based on a cDNA from *Escherichia coli*.

23. A method of nanopore sequence basecalling, comprising:
providing a membrane defining a pore wherethrough a biomolecule is threaded to generate raw nanopore sequencing data;
receiving the raw nanopore sequencing data comprising a plurality of continuous data acquisition (DAC) values corresponding to the biomolecule;
normalizing the raw nanopore sequencing data to generate normalized nanopore sequencing data comprising a plurality of normalized DAC values in a streaming manner;
generating a vector of transformed probability values using a first neural network (NN), and a normalized DAC value of the plurality of normalized DAC values, wherein the first NN comprises a first recurrent neural network (RNN), wherein the first RNN comprises a first plurality of long short term memory (LSTM) layers, wherein a LSTM layer of the first plurality of LSTM layers comprises a first unidirectional LSTM layer, wherein the first unidirectional LSTM is followed by one or more fully connected layers; and
determining a base in the biomolecule using a second NN and the generated vector of transformed probability vectors, wherein the second NN comprises a second RNN, wherein the second RNN comprises a second plurality of long short term memory (LSTM) layers, and wherein a LSTM layer of the second plurality of LSTM layers comprises a second unidirectional LSTM layer, wherein the second unidirectional LSTM is followed by one or more fully connected layers.

24. The method of claim 23, further comprising: segmenting the plurality of normalized DAC values into a plurality of discrete events,
wherein a position of the vector corresponds to an oligonucleotide, wherein a transformed probability value, of the transformed probability values of the vector, at the position of the vector comprises a probability of the oligonucleotide being represented by the DAC value, wherein a discrete event is associated with an event vector of averaged transformed probability values, wherein a position of the event vector corresponds to the oligonucleotide, and wherein an averaged transformed probability of the oligonucleotide comprises an averaged probability of the oligonucleotide being represented by DAC values of the plurality of DAC values within the event.

* * * * *